(12) United States Patent
Ewers et al.

(10) Patent No.: US 7,473,221 B2
(45) Date of Patent: *Jan. 6, 2009

(54) SURGICAL ACCESS APPARATUS AND METHOD

(75) Inventors: Richard C. Ewers, Fullerton, CA (US); John R. Brustad, Dana Point, CA (US); Edward D. Pingleton, Laguna Niguel, CA (US); Nabil Hilal, Laguna Niguel, CA (US); Gary R. Dulak, Newport Beach, CA (US); Payam Adlparvar, Lake Forest, CA (US); Robert R. Bowes, Aliso Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 10/381,220

(22) PCT Filed: Sep. 21, 2001

(86) PCT No.: PCT/US01/29682

§ 371 (c)(1),
(2), (4) Date: Mar. 20, 2003

(87) PCT Pub. No.: WO02/34108

PCT Pub. Date: May 2, 2002

(65) Prior Publication Data

US 2004/0015185 A1    Jan. 22, 2004

(51) Int. Cl.
*A61B 1/32* (2006.01)
(52) U.S. Cl. ...................................... 600/208
(58) Field of Classification Search ............... 606/1, 606/191, 108, 213; 604/164.04, 288.02; 600/206, 208
See application file for complete search history.

(56) References Cited

U.S. PATENT DOCUMENTS 558,364 A     4/1896 Doolittle
(Continued)

FOREIGN PATENT DOCUMENTS

IE        S950055        1/1994
(Continued)

OTHER PUBLICATIONS

Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.
(Continued)

*Primary Examiner*—Todd E Manahan
*Assistant Examiner*—Tuan V Nguyen
(74) *Attorney, Agent, or Firm*—David G. Majdali; Kenneth K. Vu; Richard L. Meyers

(57) ABSTRACT

A surgical access device includes a single valve forming a seal with the body wall and providing an access channel into a body cavity. The valve has properties for creating a zero-seal in the absence of an instrument and an instrument seal with instruments. The valve can include a gel comprised of an elastomer and oil providing elongation greater than 1000 percent and durometer less than 5 Shore A. The single valve can be used as a hand port where the instrument comprises the arm of a surgeon. A method for making the surgical access device includes combining a gelling agent with oil, preferably in a molding process. A method for using the device includes creating an opening with the instrument. An organ can be removed from the body cavity through the single valve to create an organ seal while the organ is addressed externally of the body cavity.

23 Claims, 18 Drawing Sheets

U.S. PATENT DOCUMENTS

| | | | |
|---|---|---|---|
| 1,157,202 A | 10/1915 | Bates et al. | |
| 1,810,466 A | 6/1931 | Deutsch | |
| 2,305,289 A | 12/1942 | Coburg | |
| 2,478,586 A | 8/1949 | Krapp | |
| 2,812,758 A | 11/1957 | Blumenschein | |
| 2,835,253 A | 5/1958 | Borgeson | |
| 2,853,075 A | 9/1958 | Hoffman et al. | |
| 3,039,468 A | 8/1962 | Price | |
| 3,111,943 A | 11/1963 | Orndorff | |
| 3,195,934 A | 7/1965 | Parrish | |
| 3,244,169 A | 4/1966 | Baxter | |
| 3,332,417 A | 7/1967 | Blanford et al. | |
| 3,347,226 A | 10/1967 | Harrower | |
| 3,347,227 A | 10/1967 | Harrower | |
| 3,397,692 A | 8/1968 | Creager, Jr. et al. | |
| 3,402,710 A | 9/1968 | Paleschuck | |
| 3,416,520 A | 12/1968 | Creager, Jr. | |
| 3,447,533 A | 6/1969 | Spicer | 128/1 |
| 3,523,534 A | 8/1970 | Nolan | |
| 3,717,151 A | 2/1973 | Collett | |
| 3,831,583 A | 8/1974 | Edmunds et al. | |
| 3,841,332 A | 10/1974 | Treacle | |
| 3,850,172 A | 11/1974 | Cazalis | |
| 3,856,021 A | 12/1974 | McIntosh | |
| 3,860,274 A | 1/1975 | Ledstrom et al. | |
| 4,024,872 A | 5/1977 | Muldoon | |
| 4,043,328 A | 8/1977 | Cawood, Jr. et al. | |
| 4,069,913 A | 1/1978 | Harrigan | |
| 4,083,370 A | 4/1978 | Taylor | |
| 4,188,945 A | 2/1980 | Wenander | |
| 4,217,664 A | 8/1980 | Faso | |
| 4,222,126 A | 9/1980 | Boretos et al. | |
| 4,254,973 A | 3/1981 | Benjamin | |
| 4,338,937 A | 7/1982 | Lerman | |
| 4,367,728 A | 1/1983 | Mutke | |
| 4,369,284 A | 1/1983 | Chen | |
| 4,454,873 A | 6/1984 | Laufenberg et al. | |
| 4,475,548 A | 10/1984 | Muto | |
| 4,550,713 A | 11/1985 | Hyman | |
| 4,553,537 A | 11/1985 | Rosenberg | |
| 4,691,942 A | 9/1987 | Ford | |
| 4,714,749 A | 12/1987 | Hughes et al. | |
| 4,755,170 A | 7/1988 | Golden | 604/52 |
| 4,777,943 A | 10/1988 | Chvapil | |
| 4,798,594 A | 1/1989 | Hillstead | |
| 4,802,694 A | 2/1989 | Vargo | |
| 4,842,931 A | 6/1989 | Zook | |
| 4,856,502 A | 8/1989 | Ersfeld et al. | |
| 4,863,438 A | 9/1989 | Gauderer et al. | |
| 4,889,107 A | 12/1989 | Kaufman | |
| 4,895,565 A | 1/1990 | Hillstead | |
| 4,903,710 A | 2/1990 | Jessamine et al. | |
| 4,911,974 A | 3/1990 | Shimizu et al. | |
| 4,926,882 A | 5/1990 | Lawrence | |
| 4,950,223 A | 8/1990 | Silvanov | |
| 4,984,564 A | 1/1991 | Yuen | |
| 4,991,593 A | 2/1991 | LeVahn | |
| 4,998,538 A | 3/1991 | Charowsky et al. | |
| 5,009,224 A | 4/1991 | Cole | |
| 5,015,228 A | 5/1991 | Columbus et al. | 604/51 |
| 5,037,379 A | 8/1991 | Clayman et al. | |
| 5,082,005 A | 1/1992 | Kaldany | |
| 5,159,921 A | 11/1992 | Hoover | |
| 5,178,162 A | 1/1993 | Bose | |
| 5,192,301 A | 3/1993 | Kamiya et al. | 606/213 |
| 5,207,656 A | 5/1993 | Kranys | |
| 5,213,114 A | 5/1993 | Bailey, Jr. | |
| 5,259,366 A | 11/1993 | Reydel et al. | |
| 5,262,468 A | 11/1993 | Chen | |
| 5,299,582 A | 4/1994 | Potts | |
| 5,316,541 A | 5/1994 | Fischer | |
| 5,336,708 A | 8/1994 | Chen | |
| 5,350,364 A | 9/1994 | Stephens | |
| 5,353,786 A | 10/1994 | Wilk | |
| 5,366,478 A | 11/1994 | Brinkerhoff et al. | 660/213 |
| 5,368,545 A | 11/1994 | Schaller et al. | 600/37 |
| 5,380,288 A | 1/1995 | Hart et al. | |
| 5,389,080 A | 2/1995 | Yoon | |
| 5,389,081 A | 2/1995 | Castro | |
| 5,407,433 A | 4/1995 | Loomas | |
| 5,429,609 A | 7/1995 | Yoon | |
| 5,437,683 A | 8/1995 | Neumann et al. | |
| 5,441,486 A | 8/1995 | Yoon | |
| 5,456,284 A | 10/1995 | Ryan et al. | |
| 5,460,616 A | 10/1995 | Weinstein | |
| 5,476,475 A | 12/1995 | Gadberry | |
| 5,480,410 A * | 1/1996 | Cuschieri et al. | 606/213 |
| 5,486,426 A | 1/1996 | McGee et al. | |
| 5,492,304 A | 2/1996 | Smith | |
| 5,496,280 A | 3/1996 | Vandebroek | |
| 5,503,112 A | 4/1996 | Luhman et al. | |
| 5,508,334 A | 4/1996 | Chen | |
| 5,514,133 A * | 5/1996 | Golub et al. | 606/1 |
| 5,518,278 A | 5/1996 | Sampson | |
| 5,522,791 A | 6/1996 | Leyva | |
| 5,524,644 A | 6/1996 | Crook | 128/888 |
| 5,531,758 A | 7/1996 | Uschold | |
| 5,545,179 A | 8/1996 | Williamson, IV | 606/213 |
| 5,562,677 A | 10/1996 | Hildwein et al. | |
| 5,603,702 A | 2/1997 | Smith | |
| 5,628,732 A | 5/1997 | Antoon, Jr. | |
| 5,632,284 A | 5/1997 | Graether | |
| 5,634,911 A * | 6/1997 | Hermann et al. | 604/256 |
| 5,634,936 A | 6/1997 | Linden et al. | 606/213 |
| 5,634,937 A | 6/1997 | Mollenauer et al. | 606/213 |
| 5,636,645 A | 6/1997 | Ou | 128/898 |
| 5,640,977 A | 6/1997 | Leahy et al. | 128/897 |
| 5,649,550 A | 7/1997 | Crook | |
| 5,653,705 A | 8/1997 | de la Torre et al. | |
| 5,672,168 A | 9/1997 | de la Torre et al. | 106/1 |
| 5,681,341 A | 10/1997 | Lunsford et al. | |
| 5,709,664 A | 1/1998 | Vandenbroek | |
| 5,720,730 A | 2/1998 | Blake, III | |
| 5,728,103 A | 3/1998 | Picha et al. | |
| 5,741,298 A | 4/1998 | MacLeod | |
| 5,753,150 A | 5/1998 | Martin et al. | |
| 5,760,117 A | 6/1998 | Chen | |
| 5,782,817 A | 7/1998 | Franzel | |
| 5,788,676 A | 8/1998 | Yoon | |
| 5,792,119 A | 8/1998 | Marx | |
| 5,795,290 A | 8/1998 | Bridges | 600/210 |
| 5,803,919 A | 9/1998 | Hart et al. | |
| 5,803,921 A | 9/1998 | Bonadio | 606/1 |
| 5,803,923 A | 9/1998 | Singh-Derewa et al. | |
| 5,810,721 A | 9/1998 | Mueller et al. | |
| 5,813,409 A | 9/1998 | Leahy et al. | 128/897 |
| 5,814,026 A | 9/1998 | Yoon | |
| 5,819,375 A | 10/1998 | Kastner | |
| 5,832,925 A | 11/1998 | Rothrum | |
| 5,841,298 A | 11/1998 | Huang | |
| 5,853,395 A | 12/1998 | Crook et al. | 60/174 |
| 5,865,729 A | 2/1999 | Meehan et al. | |
| 5,865,807 A | 2/1999 | Blake, III | |
| 5,871,474 A | 2/1999 | Hermann | |
| 5,895,377 A | 4/1999 | Smith | |
| 5,899,208 A | 5/1999 | Bonadio | 128/897 |
| 5,904,703 A | 5/1999 | Gilson | 606/213 |
| 5,906,577 A * | 5/1999 | Beane et al. | 600/207 |
| 5,919,476 A | 7/1999 | Fischer et al. | |
| 5,947,922 A | 9/1999 | MacLeod | 604/27 |
| 5,951,588 A | 9/1999 | Moenning | |
| 5,957,913 A | 9/1999 | de la Torre | |
| 5,962,572 A * | 10/1999 | Chen | 524/474 |
| 5,964,781 A | 10/1999 | Mollenauer et al. | 606/213 |

| | | | | | | |
|---|---|---|---|---|---|---|
| 5,989,233 | A | 11/1999 | Yoon | 2004/0049099 A1 | 3/2004 | Ewers et al. |
| 5,989,266 | A | 11/1999 | Foster | 2004/0049100 A1 | 3/2004 | Butler et al. |
| 5,993,471 | A | 11/1999 | Riza | 2004/0054353 A1 | 3/2004 | Taylor |
| 5,993,485 | A | 11/1999 | Beckers | 2004/0073090 A1 | 4/2004 | Butler et al. |
| 5,997,515 | A | 12/1999 | de la Torre et al. .......... 604/256 | 2004/0092796 A1* | 5/2004 | Butler et al. ................. 600/208 |
| 6,010,494 | A | 1/2000 | Schafer | 2004/0106942 A1 | 6/2004 | Taylor et al. |
| 6,024,736 | A | 2/2000 | de la Torre et al. ............... 606/1 | 2004/0127772 A1 | 7/2004 | Ewers et al. |
| 6,025,067 | A * | 2/2000 | Fay .......................... 428/314.4 | 2004/0154624 A1 | 8/2004 | Bonadio et al. |
| 6,033,426 | A | 3/2000 | Kaji ............................ 606/213 | 2004/0167559 A1 | 8/2004 | Taylor et al. |
| 6,033,428 | A | 3/2000 | Sardella ...................... 606/213 | 2004/0173218 A1 | 9/2004 | Yamada et al. |
| 6,035,559 | A | 3/2000 | Freed et al. | 2004/0254426 A1 | 12/2004 | Wenchell |
| 6,045,535 | A | 4/2000 | Ben Nun | 2004/0267096 A1 | 12/2004 | Caldwell et al. |
| 6,053,934 | A | 4/2000 | Andrews | 2005/0020884 A1 | 1/2005 | Hart et al. |
| 6,077,288 | A | 6/2000 | Shimomura | 2005/0033246 A1 | 2/2005 | Ahlberg et al. |
| 6,090,043 | A | 7/2000 | Austin et al. | 2005/0059865 A1 | 3/2005 | Kahle et al. |
| 6,142,935 | A | 11/2000 | Flom | 2005/0090717 A1 | 4/2005 | Bonadio et al. |
| 6,142,936 | A | 11/2000 | Beane et al. | 2005/0148823 A1 | 7/2005 | Vaugh et al. |
| 6,149,642 | A | 11/2000 | Gerhart et al. | 2005/0155611 A1 | 7/2005 | Vaugh et al. |
| 6,150,608 | A * | 11/2000 | Wambeke et al. ......... 174/65 G | 2005/0197537 A1 | 9/2005 | Bonadio et al. |
| 6,162,172 | A | 12/2000 | Cosgrove et al. ............. 600/208 | 2005/0222582 A1 | 10/2005 | Wenchell |
| 6,224,612 | B1 | 5/2001 | Bates | 2005/0241647 A1 | 11/2005 | Nguyen et al. |
| 6,238,373 | B1 | 5/2001 | de la Torre | 2005/0261720 A1 | 11/2005 | Caldwell et al. |
| 6,254,533 | B1 | 7/2001 | Fadem et al. | 2005/0267419 A1 | 12/2005 | Smith |
| 6,254,534 | B1 * | 7/2001 | Butler et al. ................. 600/208 | 2005/0283050 A1 | 12/2005 | Gundlappalli et al. |
| 6,276,661 | B1 | 8/2001 | Laird | 2005/0288558 A1 | 12/2005 | Ewers et al. |
| 6,287,280 | B1 | 9/2001 | Lampropoulos | 2006/0030755 A1 | 2/2006 | Ewers et al. |
| 6,319,246 | B1 * | 11/2001 | de la Torre et al. ............... 606/1 | 2006/0047284 A1 | 3/2006 | Gresham |
| 6,325,384 | B1 | 12/2001 | Berry, Sr. et al. | 2006/0052669 A1 | 3/2006 | Hart |
| 6,382,211 | B1 | 5/2002 | Crook | 2006/0084842 A1 | 4/2006 | Hart et al. |
| 6,383,162 | B1 | 5/2002 | Sugarbaker | 2006/0129165 A1 | 6/2006 | Edoga et al. |
| 6,413,244 | B1 | 7/2002 | Bestetti | 2006/0149137 A1 | 7/2006 | Pingleton et al. |
| 6,440,063 | B1 | 8/2002 | Beane et al. | 2006/0149306 A1 | 7/2006 | Hart et al. |
| 6,450,983 | B1 | 9/2002 | Rambo | 2006/0161050 A1 | 7/2006 | Butler et al. |
| 6,482,181 | B1 | 11/2002 | Racenet | | | |
| 6,485,435 | B1 | 11/2002 | Bakal | | | |

FOREIGN PATENT DOCUMENTS

| | | | | | | |
|---|---|---|---|---|---|---|
| 6,533,734 | B2 | 3/2003 | Corley, III et al. | | | |
| 6,551,344 | B2 | 4/2003 | Thill | IE | S940613 | 8/1994 |
| 6,579,281 | B2 | 6/2003 | Palmer | IE | S940960 | 12/1994 |
| 6,582,364 | B2 | 6/2003 | Butler et al. | IE | 930649 | 3/1995 |
| 6,589,167 | B1 | 7/2003 | Shimomura et al. | IE | 930650 | 3/1995 |
| 6,589,211 | B1 * | 7/2003 | MacLeod ............... 604/164.06 | IE | S71634 | 2/1997 |
| 6,613,952 | B2 | 9/2003 | Rambo | IE | S950266 | 2/1997 |
| 6,623,426 | B2 | 9/2003 | Bonadio et al. | IE | S75368 | 8/1997 |
| 6,702,787 | B2 | 3/2004 | Racenet et al. | IE | S960196 | 8/1997 |
| 6,723,044 | B2 | 4/2004 | Pulford et al. | IE | S970810 | 11/1997 |
| 6,814,078 | B2 | 11/2004 | Crook | IE | 990218 | 11/2000 |
| 6,846,287 | B2 | 1/2005 | Bonadio et al. | IE | 990219 | 11/2000 |
| 6,866,861 | B1 | 3/2005 | Luhman | IE | 990220 | 11/2000 |
| 6,895,965 | B2 | 5/2005 | Scarberry et al. | IE | 990660 | 2/2001 |
| 6,902,541 | B2 | 6/2005 | McNally et al. | IE | 990795 | 3/2001 |
| 6,908,430 | B2 | 6/2005 | Caldwell et al. | IE | S940150 | 2/2004 |
| 6,939,296 | B2 | 9/2005 | Ewers et al. | JP | 02003 235879 A | 8/2003 |
| 6,945,932 | B1 | 9/2005 | Caldwell et al. | WO | WO 95/07056 | 3/1995 |
| 6,958,037 | B2 | 10/2005 | Ewers et al. | WO | WO95/07056 | 3/1995 |
| 6,972,026 | B1 | 12/2005 | Caldwell et al. | WO | WO95/22289 | 8/1995 |
| 6,997,909 | B2 | 2/2006 | Goldberg | WO | WO 95/24864 | 9/1995 |
| 7,033,319 | B2 | 4/2006 | Pulford et al. | WO | WO 95/27468 | 10/1995 |
| 7,052,454 | B2 | 5/2006 | Taylor | WO | WO 97/11642 | 4/1997 |
| 7,081,089 | B2 | 7/2006 | Bonadio et al. | WO | WO 98/19853 | 5/1998 |
| 7,214,185 | B1 | 5/2007 | Rosney | WO | WO 98/35614 | 8/1998 |
| 2001/0037053 | A1 | 11/2001 | Bonadio et al. ............. 600/208 | WO | WO 98/48724 | 11/1998 |
| 2001/0047188 | A1 * | 11/2001 | Bonadio et al. ............. 606/213 | WO | WO 99/25268 | 5/1999 |
| 2002/0002324 | A1 | 1/2002 | McManus | WO | WO 00/32116 | 6/2000 |
| 2002/0038077 | A1 | 3/2002 | de la Torre et al. | WO | WO 00/35356 | 6/2000 |
| 2002/0072762 | A1 | 6/2002 | Bonadio et al. | WO | WO 00/32120 | 8/2000 |
| 2002/0156432 | A1 | 10/2002 | Racenet | WO | WO00/54675 | 9/2000 |
| 2003/0040711 | A1 | 2/2003 | Racenet et al. | WO | WO00/54676 | 9/2000 |
| 2003/0139756 | A1 | 7/2003 | Brustad | WO | WO00/54677 | 9/2000 |
| 2003/0187376 | A1 | 10/2003 | Rambo | WO | WO01/08581 | 2/2001 |
| 2003/0192553 | A1 | 10/2003 | Rambo | WO | WO 01/26559 | 4/2001 |
| 2003/0225392 | A1 | 12/2003 | McMichael et al. | WO | WO02/34108 | 5/2002 |
| 2004/0015185 | A1 | 1/2004 | Ewers et al. | WO | WO03/032819 | 4/2003 |
| 2004/0024363 | A1 | 2/2004 | Goldberg | | | |

| | | |
|---|---|---|
| WO | WO03/034908 | 5/2003 |
| WO | WO03/061480 | 7/2003 |
| WO | WO 03/077726 | 9/2003 |
| WO | WO 03/103548 | 12/2003 |
| WO | WO 2004/075730 A2 | 9/2004 |
| WO | WO 2004/075730 A3 | 9/2004 |
| WO | WO 2004/075741 A2 | 9/2004 |
| WO | WO 2004/075741 A3 | 9/2004 |
| WO | WO 2004/075930 A2 | 9/2004 |
| WO | WO 2004/075930 A3 | 9/2004 |
| WO | WO 2005/034766 | 4/2005 |
| WO | WO 2005/034766 A2 | 4/2005 |

OTHER PUBLICATIONS

Horigane, et al., Technical Note: Development of a Duodenal Cannula for Sheep, Journal of Animal Science, Apr. 1992, vol. 70, Issue 4, pp. 1216-1219.

Horigane, et al., Silicone Rumen Cannula with a Soft Cylindrical Part and a Hard Flange, Journal of Dairy Science, Nov. 1989, vol. 72, No. 11, pp. 3230-3232.

McSweeney, Cannulation of the Rumen in Cattle and Buffaloes, Australian Veterinary Journal, Aug. 1989, vol. 66, No. 8, pp. 266-268.

Yamazaki et al., Diurnal Changes in the Composition of Abomasal Digesta in Fasted and Fed Sheep, The Tohoku Journal of Agricultural Research, Mar. 1987, vol. 37, No. 3-4, pp. 49-58.

Dexterity Protractor Instruction Manual by Dexterity Surgical, Inc.

Co-Pending U.S. Appl. No. 11/755,305, filed May 30, 2007; Title: Wound Retraction Apparatus and Method.

Co-Pending U.S. Appl. No. 10/516,198, filed Nov. 30, 2004; Title: Wound Retractor.

Co-Pending U.S. Appl. No. 10/927,551, filed Aug. 25, 2004; Title: Surgical Access System.

Co-Pending U.S. Appl. No. 11/244,647, filed Oct. 5, 2005; Title: Surgical Access Apparatus and Method.

Co-Pending U.S. Appl. No. 11/245,709, filed Oct. 7, 2005; Title: Surgical Access System.

Co-Pending U.S. Appl. No. 11/330,661, filed Jan. 12, 2006; Title: Sealed Surgical Access Device.

Co-Pending U.S. Appl. No. 11/548,746, filed Oct. 12, 2006; Title: Method of Making a Hand Access Laparoscopic Device.

Co-Pending U.S. Appl. No. 11/548,758, filed Oct. 12, 2006; Title: Split Hoop Wound Retractor With Gel Pad.

Co-Pending U.S. Appl. No. 11/548,765, filed Oct. 12, 2006; Title: Split Hoop Wound Retractor.

Co-Pending U.S. Appl. No. 11/548,767, filed Oct. 12, 2006; Title: Circular Surgical Retractor.

Co-Pending U.S. Appl. No. 11/548,781, filed Oct. 12, 2006; Title: Wound Retractor With Gel Cap.

Co-Pending U.S. Appl. No. 11/548,955, filed Oct. 12, 2006; Title: Hand Access Laparoscopic Device.

Co-Pending U.S. Appl. No. 11/564,409, filed Nov. 29, 2006; Title: Surgical Instrument Access Device.

European Patent Office, Supplementary European Search Report for European Application No. EP 01 97 3379, dated Jul. 5, 2007, based on International Patent Application No. PCT/US01/29682.filed Sep. 21, 2001.

US 5,344,646, Chen. (withdrawn).

Co-Pending U.S. Appl. No. 10/381,220, filed Mar. 20, 2003; Title: Surgical Access Apparatus and Method.

US Patent Office, International Search Report and The Written Opinion of the International Searching Authority for PCT Application No. PCT/US2004/05484.

European Patent Office, International Search Report and The Written Opinion of the International Searching Authority for PCT Application No. PCT/US2006/039799 mailed Mar. 27, 2007.

European Patent Office, International Search Report and The Written Opinion of the International Searching Authority for PCT Application No. PCT/US2006/039800 mailed Apr. 16, 2007.

European Patent Office, International Search Report and Written Opinion of the International Searching Authority for International Application No. PCT/US2006/039883, mailed Jan. 31, 2007.

European Patent Office, International Search Report and Written Opinion of the International Searching Authority for International Application No. PCT/US2006/039905 mailed Jan. 17, 2007.

European Patent Office, International Search Report and The Written Opinion of the International Searching Authority for International Application No. PCT/US2006/040073 Jan. 26, 2007.

European Patent Office, International Search Report and The Written Opinion of the International Searching Authority for International Application No. PCT/US2006/040154 mailed Jan. 30, 2007.

International Search Report and Written Opinion of the International Searching Authority for PCT application No. PCT/US01/29682.

Technical Note: Development of a Duodenal Cannula for Sheep, Faculty of Agriculture and Schol of Medicine Tohoku University, Sendai 981, Japan.

The International Bureau of WIPO, International Preliminary Report on Patentability, dated Aug. 29, 2006, for international application No. PCT/US2004/028250.

The International Bureau of WIPO, International Preliminary Report on Patentability dated Apr. 16, 2008 for PCT Application No. PCT/US2006/039799.

The International Bureau of WIPO, International Preliminary Report on Patentability for International Application No. PCT/US2006/039800 dated Apr. 16, 2008.

* cited by examiner

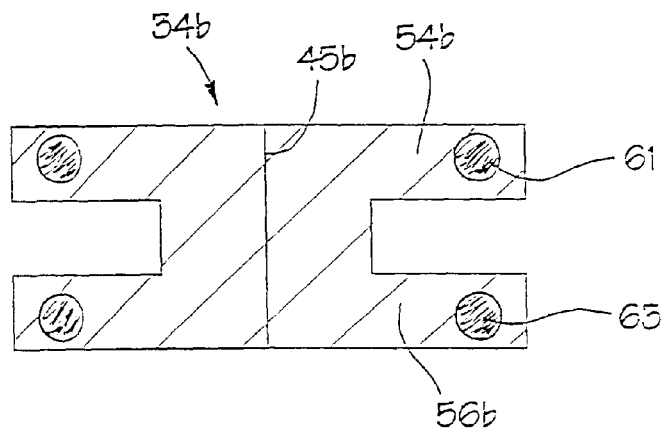
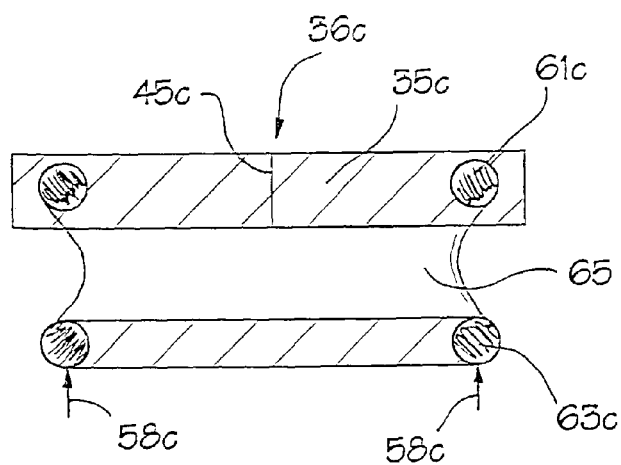
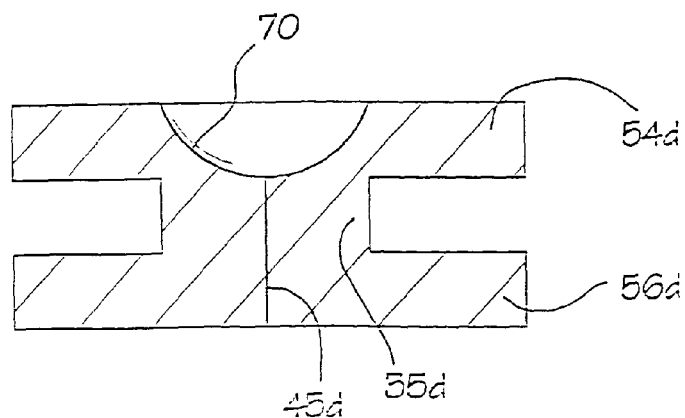

SURGICAL ACCESS APPARATUS AND METHOD

BACKGROUND OF THE INVENTION

1. Field of the Invention

This invention relates generally to devices and other apparatus facilitating sealed access with surgical instruments such as a surgeon's hand, across a body wall and into a body cavity.

2. Background of the Invention

In several areas of surgery there exists a need to have mechanisms or devices that can seal a body cavity or space, and yet permit the introduction of surgical instruments such as guidewires, endoscopes, and even the hand of a surgeon. Typical of these areas of surgery is laparoscopic surgery which relies on surgical instruments inserted through the abdominal wall to reach an operative site within the abdominal cavity. In order to increase space around the operative site within the cavity, insufflation gases are typically introduced to inflate the cavity and elevate the abdominal wall. This pressurizing of the abdominal cavity is referred to as pneumoperitoneum. In this context, the need to seal the body cavity or space arises from the need to maintain the pneumoperitoneum even when instruments are present.

Trocars have been commonly used to provide instrument access in laparoscopic surgeries. These trocars have included elaborate seal structures having zero seals which prevent escape of the gases in the absence of instruments, and instrument seals which prevent escape of the gases in the presence of instruments. Unfortunately, the instrument seals have been able to accommodate only a narrow range of instrument diameters. Where wider ranges were desired multiple seal pairs had to be provided.

Some instruments, such as the hand of the surgeon, have been too large for trocar access. Under these circumstances, hand-assisted laparoscopic seals have been provided. Such devices have been large, cumbersome, and largely ineffective in providing the required sealing mechanism. Other access devices, such as Touhy-Borst seals, have been used but only for very small diameter access such as that required by a guidewire.

Each of the prior devices suffers from drawbacks which make the device difficult or cumbersome to use. For example, a Touhy-Borst seal requires two hands to use and does not form a seal when a guidewire or other device is about to be introduced. Present trocar seals and hand-assisted seals require two valves, one forming an instrument seal in the presence of the instrument, and the other forming a zero seal in the absence of the instrument. For example, in hand-assisted devices, elaborate mechanisms have been required to seal around the surgeon's arm. When the arm is removed, a separate zero seal has been required to prevent the escape of blood or insufflation gases.

SUMMARY OF THE INVENTION

These deficiencies of the prior art are overcome with the present invention which includes both a seal apparatus and a method for using this apparatus to perform elaborate surgeries. In one embodiment, the device includes a valve structure formed of a gel including, for example, a thermoplastic base such as KRATON (a trademark of Shell Corporation) and an oil. The resulting elastomer has an excellent tear strength, elongation greater than 1,000 percent, a very low durometer or hardness, and biocompatibility. A process for manufacturing this device is greatly simplified using molding techniques.

Importantly, the access device can function as both a zero seal and an instrument seal. Furthermore, it can accommodate a full range of instrument diameters, such as a range from two French in the case of a guidewire, to three or four inches in the case of a surgeon's hand. In addition, several instruments can be accommodated at the same time with a single access device.

Both tear resistance and sealing capability can be enhanced by encapsulating the gel in a sheath or otherwise providing circumferential reinforcement for the valve structure. Additives can be provided either on or in the gel to enhance properties such as lubricity, appearance, wound treatment and/or protection, anti-cancer protection and anti-microbial protection. Additional chemicals, compounds, pharmaceuticals or even mechanical devices can be mixed with or embedded in the gel material to vary chemical, pharmaceutical or physical properties of the access device.

These and other features and advantageous of the invention will be clarified with a description of preferred embodiments and reference to the associated drawings.

DESCRIPTION OF THE DRAWINGS

FIG. 9 is a cross section view similar to FIG. 8 and illustrating an embodiment with circumferential reinforcement members;

FIG. 10 is an axial cross section view similar to FIG. 9 and illustrating a double-ring retractor with an access device of the present invention;

FIG. 11 is a radial cross section view similar to FIG. 8 and illustrating an embodiment having a lead-in cavity or pocket;

FIG. 39 is a top plan view showing use of a template;

FIG. 40 is a top plan view of showing placement of the retraction sheath;

FIG. 41 is a top plan view showing placement of the base ring and securement of the traction sheath; and FIG. 42 is an axial cross section view partially in section showing placement of the gel cap relative to the base.

DESCRIPTION OF PREFERRED EMBODIMENTS AND BEST MODE OF THE INVENTION

Figure 1:
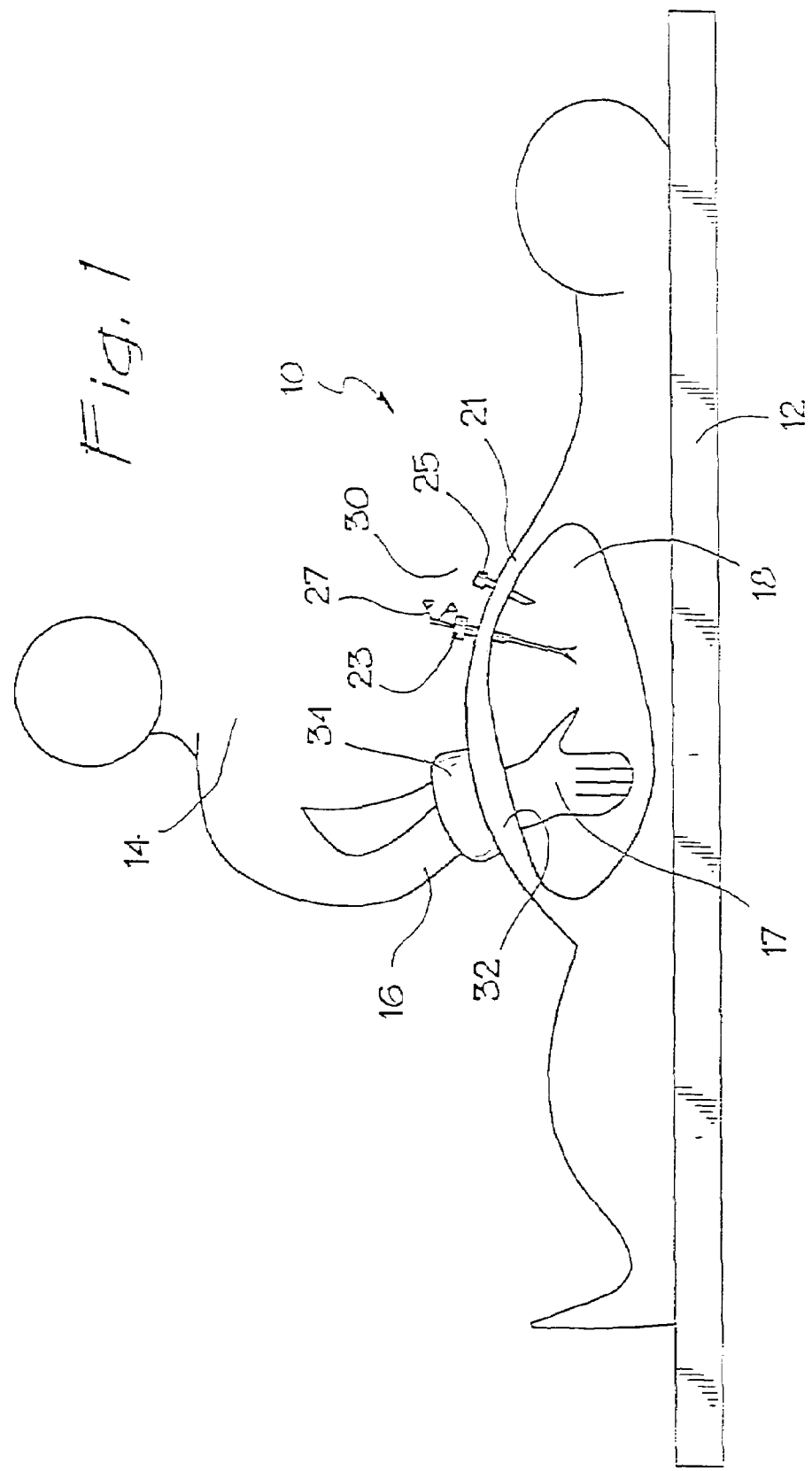
FIG. 1 is a perspective view showing a patient prone on an operating table with his abdomen insufflated, and with instrument access provided by trocars and the access device of the present invention.

A patient is illustrated in FIG. 1 and designated generally by the reference numeral 10. The patient 10 is shown in a prone position on an operating table 12, where abdominal surgery is being performed by a surgeon 14 having an arm 16 and a hand 17. In the illustrated example, the operative procedure is performed within an abdominal cavity 18 with instrument access provided through an abdominal wall 21. In this type of operation, commonly referred to as laparoscopic surgery, trocars 23 and 25 are commonly used to provide minimally invasive access through the abdominal wall 21 for instruments such as a grasper 27 and an endoscope 30

Although the specific focus of this disclosure will be on a preferred laparoscopic procedure, it will be noted that laparoscopic surgery is merely representative of a type of operation wherein a procedure can be performed in a body cavity with minimal access through a body wall.

Notwithstanding the foregoing generality, it is important to note that with respect to laparoscopic surgery, it is often desirable that the surgeon 14 be able to insert his/her hand 17 through the abdominal wall 21 and into the abdominal cavity 18. This insertion of the hand 17 provides the surgeon 14 with direct access to various elements of the anatomy In order to accommodate the hand 17 and arm 16, of the surgeon 14, a small incision 32 is typically created in the abdominal wall 21. An access device 34 of the present invention can be provided to further facilitate this access by the hand of the surgeon 14.

Particularly in the case of laparoscopic surgery, it is advantageous to insufflate the abdominal cavity 18 with a gas, such as carbon dioxide, in order to elevate the abdominal wall 21 and thereby increase the volume of the working space within the cavity 18. Maintenance of this insufflation pressure, commonly referred to as pneumoperitoneum, is particularly difficult where access is desired across the abdominal wall 21, for example, through the trocars 23, 25, as well as the access device 34. For this reason, a substantial effort has been directed to providing such access devices with sealing characteristics both in the presence of instruments and in the absence of instruments, such as the grasper 29, scope 30 and hand 27.

Thus, the trocars 23 and 25 have typically been provided with complex valve structures, including, for each narrow range of instrument sizes, an instrument valve which forms an instrument seal in the presence of an instrument, and a zero valve which forms a zero seal in the absence of an instrument. By providing both an instrument seal and a zero seal the valve structures have been able to inhibit the escape of gases through the trocars both in the presence and the absence of an instrument, respectively.

The instrument seals have been particularly cumbersome, as noted, and have only been effective for a small range of instrument diameters. For example, separate instrument seals have been needed for instruments, such as guidewires, which may have a diameter of only two French to three French. For medium-sized instruments having diameters of three millimeter to five millimeters, a second instrument seal has been required. In some cases, even a third instrument seal has been necessary in order to accommodate instruments having diameters such as nine millimeters to 12 millimeters. Typically the varying sizes of instruments have also required individual zero seals for each range. Thus, in a complex trocar, such as the trocar 23, there might be as many as six separate seals associated with the access device.

Were it not for the desire to maintain the pneumoperitoneum, there would be no need for the trocars 23, 25 or the access device 34. One would merely cut an incision in the abdominal wall 21 and insert the instrument directly through the incision. However, without appropriate valves or seals, the insufflation gases would merely escape through the incisions. This would be particularly detrimental in the case of the incision 32 which must be sufficiently large to accept the hand 17 of the surgeon 14. Thus it is a primary purpose of the access device 34 to form with the incision 32 an access or working channel 34, and to provide a valve or other sealing structure across the working channel 34 in order to maintain the pneumoperitoneum.

Figure 2:
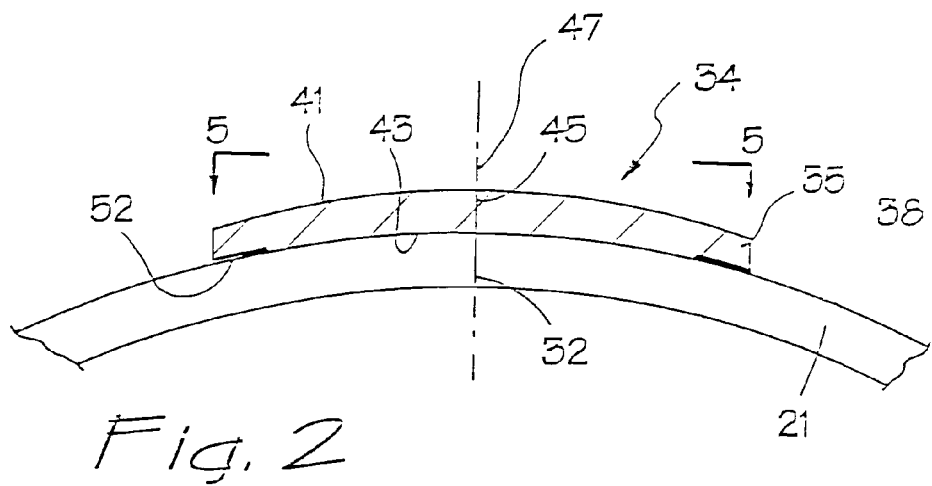
FIG. 2 is an enlarged side elevation view of the access device of FIG. 1 operatively disposed exteriorly as the abdominal wall.

An enlarged view of one embodiment of the access device 34 is illustrated in FIG. 2 which also shows the abdominal wall 21 and the incision 32. In this simple form, the access device 34 has the general configuration of a pad 35, meaning that it is generally flat and disposed in a plane such as the plane 38. Typically parallel to this plane 38 are a pair of major surfaces of 41 and 43 which provide the pad 35 with a substantial surface area. An opening or slit 45 can be formed through the pad 35, generally along an axis 47 perpendicular to the plane 38.

Figure 3:
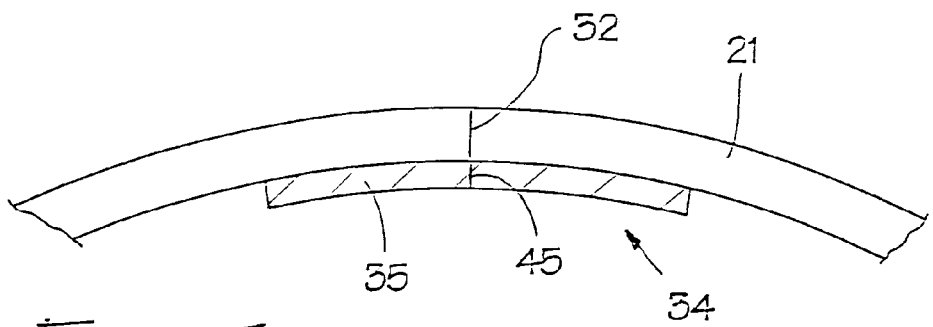
FIG. 3 is a side elevation view similar to FIG. 2 showing the access device operatively disposed interiorly of the abdominal wall.
Figure 4:
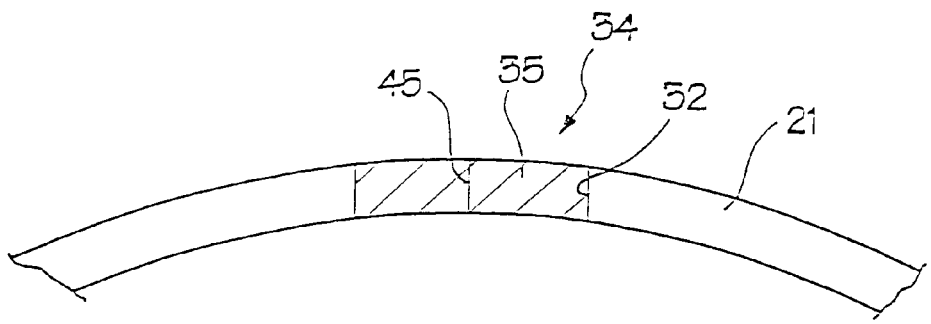
FIG. 4 is a side elevation view similar to FIG. 2 showing the access device operatively disposed within an incision in the abdominal wall.

When operatively disposed, the opening 45 of the pad 35 is in communication with the incision 32 and, in this case, forms with the incision 32, the working channel 36. The alignment of the opening 45 and incision 32 can occur with the pad 35 disposed exteriorly of the abdominal wall as illustrated in FIG. 2, interiorly of the abdominal wall is 21 as illustrated in FIG. 3, or within the abdominal wall 21 as illustrated in FIG. 4. In any of these positions, operative disposition of the pad 35 relative to the abdominal wall 21 requires that the pad 35 be maintained in its operative position and that it form a seal around the incision 32. Referring to the plan view of FIG. 5, these two functions are accomplished with an adhesive 50 disposed around the incision 32 between the pad 35 and the abdominal wall 21.

Figure 5:
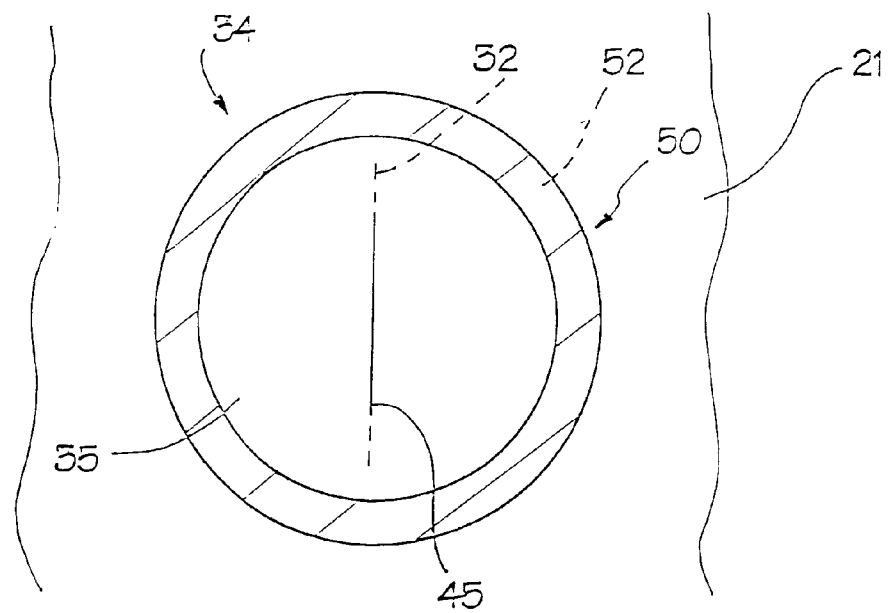
FIG. 5 is a plan view taken along lines 5-5 of FIG. 2.

If this adhesive 50 is formed as a continuous ring 52, as illustrated in FIG. 5, the pad 35 can be disposed with the ring 52 positioned circumferentially around the incision 32 to form a seal between the pad 35 and the abdominal wall 21. In the illustrated example, when the pad 35 is operatively positioned, the escape of insufflation gases is inhibited between the pad 35 and the abdominal wall 21 by the adhesive ring 52.

The escape of insufflation gases is inhibited through the opening 45 of the pad 35 by the self-sealing characteristics of the material forming the pad 35. This material and its highly advantageous properties are discussed in significant detail below.

It will be appreciated that the functions of the adhesive ring 52 can be accomplished in many different ways using many different materials and shapes. For example, many materials other than adhesives can be used to maintain the pad 35 in position over the incision 32. The formation of a seal around the incision 32 can also be accomplished with methods other than adhesion. Furthermore, the shape of the continuous seal formed by the adhesive 50 need not be in the shape of a circle. Rather, any continuous pattern sufficiently large to form a perimeter around the incision 32 could facilitate the desired sealing relationship. Finally, it will be noted that the mere placement of the pad 35, for example, interiorly of the abdominal wall 21 as illustrated in FIG. 3, may produce a perimeter seal merely as a result of the insufflation pressure.

Figure 6:
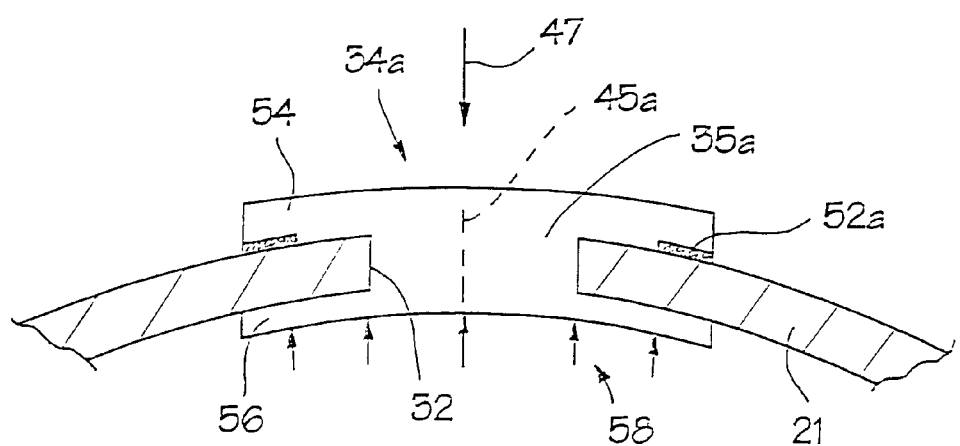
FIG. 6 is a side elevation view similar to FIG. 2 and illustrating a further embodiment of the access device having an external flange and an internal flange.

A further embodiment of the access device 32 is illustrated in FIG. 6 where elements of structure similar to those previously disclosed or designated with the same reference numeral followed by the lower case "a." In this embodiment, the functions of position-maintenance and sealing are accomplished with an alternative configuration for the access device itself. The pad 35 in this case is disposed within the incision 32 as illustrated in FIG. 4. However, an external flange 54 and an internal flange 56 are formed integral with the pad 35.

When operatively disposed, the external flange 54 is positioned outside of the abdominal wall 21 while the internal flange 56 is disposed interiorly of the abdominal wall 21a. In this matter, the pad 35 can be disposed within the incision 32a and held in position by the flanges 54, 56. When the hand 17 of the surgeon 14 is inserted through the access device 34, the exterior flange 54 prevents the pad 35a from moving distally. Similarly, when the hand 17 of the surgeon 14 is withdrawn, the interior flange 56 prevents the pad 35a from moving proximally In this embodiment, the opening 45a extends through the pad 35a as well as the flanges 54 and 56, and completely defines the working channel 34 through the incision 32.

The primary seal which is required between the access device 34a and the abdominal wall 21, can be formed with the adhesive ring 52a as discussed with reference to FIG. 6. Alternatively, this embodiment including the interior flange 56 may rely merely upon the surface contact between the flange 56a and the abdominal wall 21. In this case, the primary seal can be formed between these structural elements and enhanced by the pneumoperitoneum pressure which forces the interior flange 56 against the abdominal wall as illustrated by a plurality of arrows 58. This seal is formed primarily in a radial plan generally perpendicular to the axis 47.

The function of the primary seal may be further enhanced by additional sealing which occurs between the pad 35a and the portions of the abdominal wall 21 forming the incision 32. In this location, the abdominal wall 21 is radially compressed by the mere presence of the pad 35 within the incision 32. The resulting pressure produces an axial seal between the pad 35a and the abdominal wall 21.

If the adhesive ring 52a is desired for this embodiment, it is most advantageously placed around the incision 32, between the exterior flange 54 and the abdominal wall 21.

It will be noted that whenever an instrument, such as the arm 16 or hand 17 of the surgeon 14, is inserted through the pad 35, the material of the pad conforms to the surface of the instrument and forms the instrument seal with the instrument.

Accordingly, during the entire period beginning with insertion of the instrument and ending with withdrawal of the instrument, there is substantially no loss of insufflation gas through the pad 35a nor any loss of pneumoperitoneum within the abdominal cavity 18.

Figure 7:
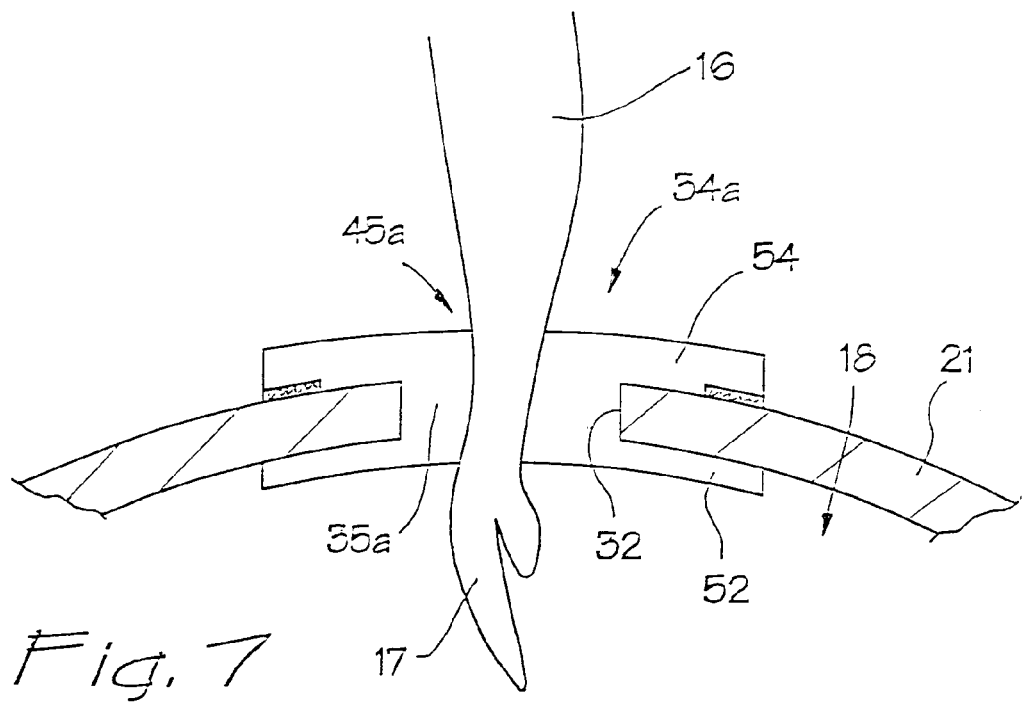
FIG. 7 is a side elevation view similar to FIG. 6 and illustrating the hand of a surgeon being inserted through the access device.

With further reference to FIG. 7, it will be appreciated that the arm 16 and hand 17 of the surgeon 14 are merely examples of instruments which can be inserted through the access device 34a. In the absence of the instrument, or hand 17 in the case of FIG. 7, the opening or slit 45a merely closes against itself to form a zero seal, thus preventing the escape of insufflation gases through the access device 34a. When the instrument, such as the hand 17, is inserted through the opening or slit 45a, an instrument seal is formed between the material of the access device 34a and the exterior surface of the instrument. This prevents the escape of insufflation gases through the access device 34a, even when an instrument is present. Thus, insufflation pressures can be maintained within the abdominal cavity 18 whether or not the instrument is in place. Note that these seals, the zero seal and the abdominal seal, can be formed as a single valve structure having properties for accommodating a full range of instrument sizes.

Formation of the pad 35a will typically be accomplished in a simple molding process described in greater detail below. In such a process, the opening or slit 45a may be formed as part of the molding process.

In most cases, the single access opening 45a will be sufficient to accommodate the operative procedure. However, a further advantage of the access device 34a will be particularly appreciated by the surgeon 14 who requires even more access through the pad 35a. Consider for example, the surgeon 14 having his/her arm 16 inserted through the opening 45a when he/she decides that a further instrument is required for the operative procedure. Under these circumstances, a further opening through the pad 35a can be established by merely inserting the desired operative instrument through the pad 35a. In this manner, the instrument can create its own access hole beside the primary opening 45a.

Particularly for those operative instruments having pointed distal ends, the instrument can merely be forced through the pad 35a forming its own access hole, such as the opening 45a, as it is moved distally. This opening, created by the operative instrument itself, would automatically form an instrument seal as the instrument is inserted, as well as a zero seal as the instrument is withdrawn.

For operative instruments not having pointed distal ends, it is possible to form a new access hole using a secondary instrument, such as a trocar obturator. After the access hole is formed, the obturator can be removed, vacating the access hole to receive the operative instrument. Throughout this process of initially forming an access hole and ultimately inserting an operative instrument through the hole, both zero seals and instrument seals are formed to maintain the pneumoperitoneum.

With the advantages associated with 1) the formation of an instrument seal and a zero seal with a single valve accommodating a wide range of diameters, and 2) the formation of an instrument opening using the instrument itself, it will be appreciated that the concept of this invention will typically be embodied with a structure that is particularly dependent upon the material which forms the access device 34. In a preferred embodiment, the pad 35 is formed of a KRATON/oil mixture including a KRATON Tri-block with a Styrene-Ethylene/Butylene-Styrene (S-E/B-S) structure in combination with a mineral oil. Other tri-block polymers can be used for this application such as Styrene-Isoprene-Styrene, (S-I-S), Styrene-Butadiene-Styrene (S-B-S), Styrene-Ethylene/Propylene-Styrene (S-E/P-S) manufactured under the trademark SEPTON by the Kuraray Co. These general formulas can be further distinguished by the ratio of the styrene to rubber content: for example, Grade 1650 is a S-E/B-S tri-block with a 29/71 styrene to rubber ratio.

In addition to tri-blocks there are also di-block versions of these materials where styrene is present at only one end of the formula, for example, Styrene-Ethylene/Butylene (S-E/B) di-block.

The various base formulas may also be alloyed with one another to achieve a variety of intermediate properties. For example KRATON G1701X is a 70% S-E/B 30% S-E/B-S mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the material of the pad 35 may also include silicone, soft urethanes and even harder plastics which might provide the desired sealing qualities with the addition of a foaming agent. The silicone materials can be of the types currently used for electronic encapsulation. The harder plastics may include PVC, Isoprene. KRATON neat, and other KRATON/oil mixtures. In the KRATON/oil mixture, for example, oils such as vegetable oils, petroleum oils and silicone oils might be substituted for the mineral oil. In the broadest sense, all of these mixtures can be described generally as a gel. The gel will typically have properties including an ability to "flow" which approaches that of a fluid. Particularly in the vicinity of any opening or slit 45 extending through the access device 34, propagation of the opening may be of concern. Stresses resulting from the presence of an instrument will be concentrated at the ends of such an opening or slit. For this reason, a good tear resistance is desired for the gel material. Such a tear resistance is often inherent in the KRATON/oil mixtures and may be enhanced by encapsulating the gel in other materials. For example, a low tear resistant gel could be encapsulated in a urethane sheath to improve the tear resistant qualities of the resulting products. Such a sheath need not be elastic but could be comprised, for example, of overlapping sheets of a non-elastic material.

Any of the gel materials contemplated could be modified to achieve different properties such as enhanced lubricity, appearance, and wound protection, or to provide anti-cancer or anti-microbial activity. Additives can be incorporated directly into the gel, for example in the case of pharmaceuticals, or applied as a surface treatment to the gel, for example, to improve lubricity or appearance. Other compounds could be added to the gel to modify its physical properties or to assist in subsequent modification of the surface by providing bonding sites or a surface charge. Antioxidants and antirads can be added to the mixture to extend the shelf life of the finished product or increase its ability to withstand radiation sterilization.

Sealing materials used in medical access devices of the past have been chosen primarily for their durometer and elongation. It is these properties which measure the ability of the material to move into small spaces and crevices as may be required to form, an instrument seal across the working channel of a trocar. For example, in the past, a silicone mixture was used in medical valves. This mixture had the following properties: an ultimate elongation less than about 1000 percent and a durometer not less than about 5 Shore A.

These properties of the prior art materials are far exceeded by the properties associated with the present invention which in some respects provide a full magnitude of advantage. In fact, the difference between the materials of the prior art and the materials of the present invention are sufficiently substantial, that it is perhaps misleading to refer to the present material as merely a gel. According, the material of the present invention, having properties including an ultimate elongation greater than about 1000 percent and a durometer less than about 5 Shore A, will be referred to herein as an "ultragel."

In a preferred embodiment of the present invention, the ultragel includes KRATON and mineral oil and provides a sealing material with the following properties: an ultimate elongation exceeding about 1500 percent, and a durometer of less than about 200 Bloom. The durometer in this case is considerably lower than that of the prior art materials. In fact, the durometer of the present material is so soft it cannot even be measured on the Shore A scale.

The resulting elongation and durometer of the present material facilitates its use with as an access valve which is capable of forming seals with a full range of instrument sizes, but is also capable of functioning as a zero seal. Whereas access devices of the prior art may have required as many as six separate seals in order to accommodate a full range of instrument sizes, access devices can now be made with only a single valve formed of the ultragel material.

In a typical manufacturing process, the KRATON G1651 is mixed with the mineral oil in a ratio by weight of 1 to 9. In order to manufacture this material, the combination is heated to a temperature of about 200° centigrade. In a preferred method of manufacturing, the mold is provided with a circumferential ring insert which is molded into the gel, and slit inserts which can be removed from the gel to form the opening or slit 45. The resulting gel can be coated with cornstarch to reduce tack and cooled at room temperature.

Many of the properties of the KRATON/oil mixture will vary with adjustments in the weight ratio of the components.

In general, the greater the percentage of mineral oil, the more fluid the mixture; the greater the percentage of KRATON, the more rigid the material. Weight ratios of KRATON to oil as low as 1 to 5 have been contemplated for a more rigid structure. As the KRATON/oil weight ratio approaches 1 to 10, the mixture becomes more liquid. Ratios as high as 1 to 15 have been contemplated for this invention.

The processing temperature can also vary considerably as it is primarily dependent on the type of KRATON used. Temperatures in a range of about 150° centigrade to about 250° centigrade have been contemplated.

With an appreciation that these ratios and temperatures can develop considerably different properties, it is now apparent that these materials can be layered to provide generally different properties within each layer. For example, an outer layer might be formed of a KRATON/oil mixture having more rigid properties, thereby providing the pad 35 with an outer lave, that is more rigid. After that layer is at least partially cured, another layer of the material can be poured inside of the outer layer. This second layer might be softer providing the pad 35 with the significant sealing properties. It has been found that successive layers will tend to fuse slightly at their interface, but will generally maintain their separate identities. Additional layers could be added to provide a progression of properties in a particular device.

Having discussed the properties desirable for the gel material, and the process of manufacture, one can now address the other embodiments of the concept which may provide additional advantages for particular surgical procedures. An embodiment of the access device 34, shown in its operative position in FIG. 6, is illustrated by itself in the axial cross section view of FIG. 8.

This same embodiment can be reinforced with o-rings 61 and 63 as illustrated in FIG. 9 where elements of structure are designated by the same reference number followed by the lower case letter "b." Providing these o-rings 61 and 63 may facilitate several functions associates with the access device 34b. For example, the rings 61, 63 will typically aid in maintaining a radial sealing pressure on all sides of the opening 45b. The rings 61 and 63 will also tend to maintain the flanges 54b and 56b respectively, in their generally planar configurations. This further ensures that the flanges 54, 56 will not collapse into the incision 32 with the insertion or withdrawal of an instrument, such as the surgeon's hand 17. Of course, the o-rings 61 and 63 must be sufficiently large to accommodate the instrument during insertion and removal.

A further embodiment of the invention is illustrated in FIG. 10, where elements of structure are similar to those previously disclosed are designated with the same reference numerals followed by the lower case letter "c." This embodiment includes the pad 35c with the opening or slit 45c. The external perimeter o-ring 61c is inserted molded into the circumference of the pad 35c. The internal o-ring 63c is coupled to the pad 35c, for example, by way of attachment to the o-ring 61c for example, by a membrane 65. In this case, the membrane 65 has a generally cylindrical configuration and elastomeric properties. In preferred embodiments, the membrane 65 is formed of urethane, neoprene or isoprene.

When the embodiment of FIG. 10 is being operatively positioned, the internal o-ring 63b is initially gathered and inserted through the incision 32 (FIG. 2). The pad 35c and external o-ring 61c are left outside the incision 32 so that the only material extending across the incision 32 is the membrane 65. It will be noted that in this case, the working channel 36c is formed by the slit 45c, the cylindrical membrane 65, and the internal o-ring 63b.

In this particular embodiment, the pad 35c functions generally as described with reference to FIG. 2. The primary seal between the pad 35c and the abdominal wall 21 can be formed either with a circumferential ring, such as the adhesive ring 52c, or by relying on the sealing characteristics of the insufflation gas against the internal o-ring 63b and membrane 65.

This embodiment of FIG. 10 is of particular advantage as it incorporates the pad 35c in perhaps its simplest configuration, while providing a primary seal between the device 34c and the abdominal wall 21 which is facilitated by the insufflation pressure. Furthermore, the membrane 65 enhances the sealing characteristics of the device 34c, and provides a lining for the incision 32. With the membrane 65, the incision 32 need not be stretched to a diameter greater than that required by any instrument inserted through the work in channel 36c.

Figure 8:
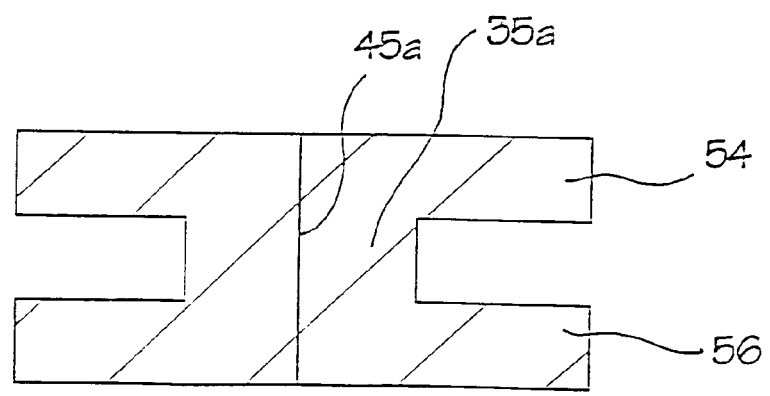
FIG. 8 is an axially cross section view of the access device illustrated in FIG. 6.

A further embodiment of the invention is illustrated in FIG. 11 where elements of structure similar to those previously disclosed are designated with the same reference numeral followed by the lower case letter "d." This embodiment is similar to that of FIG. 8 in that it includes the pad 35b, slit 45d, exterior flange 54d, and internal flange 56d. The embodiment of FIG. 11 differs from that of FIG. 8 in that it includes a lead-in cavity 70 which is in communication with the slit 45d.

In a preferred embodiment, this cavity 70 is sized and configured to receive the arm 16 of the surgeon 14 in a manner illustrated in FIG. 7. In this case, the slit 45d would function primarily to maintain a zero seal, while the portions of the pad 35d or flange 54d which form the cavity 70 would function primarily to form the instrument seal.

Figure 12:
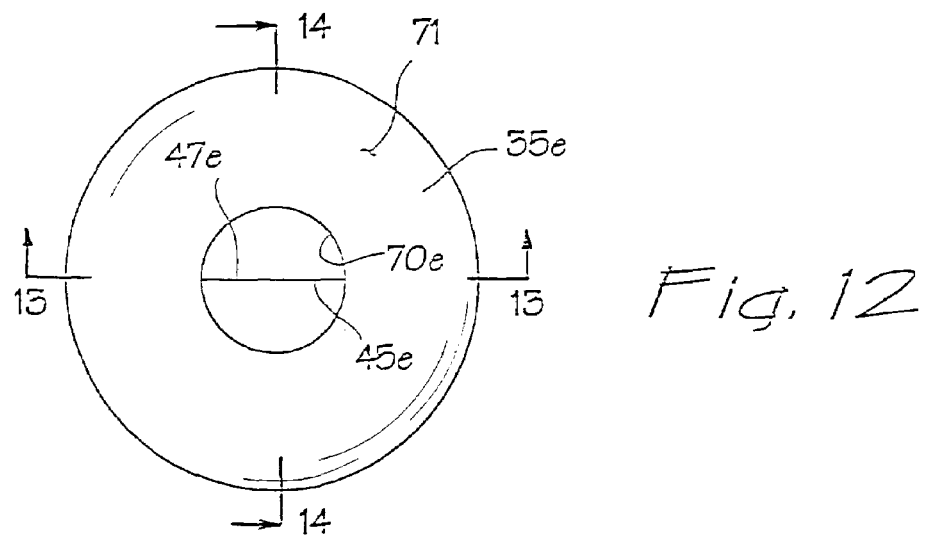
FIG. 12 is a top plan view of the embodiment illustrated in FIG. 11.
Figure 13:
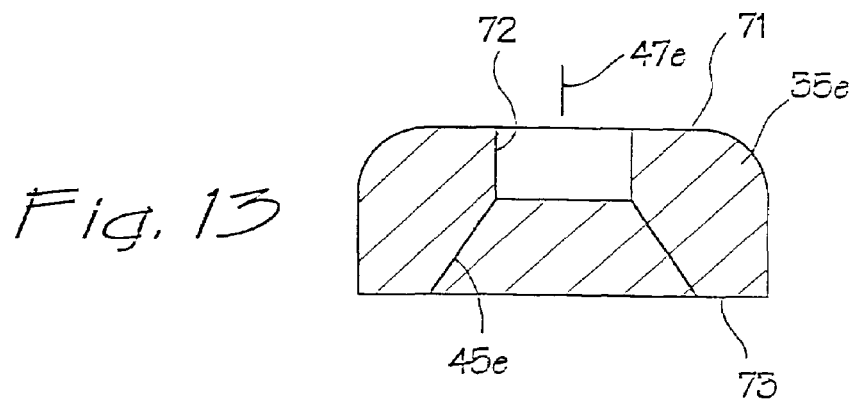
FIG. 13 is an axial cross section view taken along lines 13-13 of FIG. 12.
Figure 14:
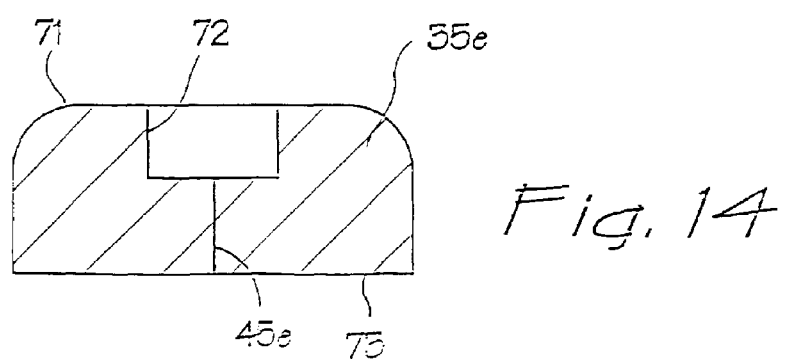
FIG. 14 is an axial cross section view taken along lines 14-14 of FIG. 12.

A further embodiment of the invention is illustrated in the plan view of FIG. 12 and the cross section views of FIGS. 13 and 14. In this embodiment, elements of structure similar to those previously discussed are designated with the same reference numeral followed by the lower case letter "e." In this case, the lead-in cavity has the general shape of a cylinder 72 with an axis that is collinear with the axis 47e of the pad 35e.

As perhaps best illustrated in FIG. 13, the slit 45e has a trapezoidal configuration. Thus, it begins proximally with a narrow length which may generally be equivalent to the diameter of the cylinder 32. From the cavity 70e, the length of the slit 45e increases with progressive positions distally through the pad 35e. In the illustrated embodiment, the trapezoidal slit 45e is formed as the frustum of an isosceles triangle.

Figure 15:
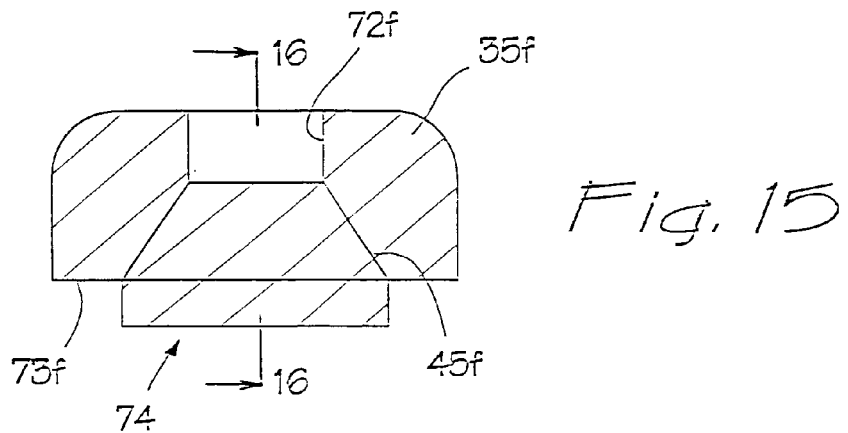
FIG. 15 is an axial cross section view similar to FIG. 13 and illustrating an embodiment with a duct-bill valve.
Figure 16:
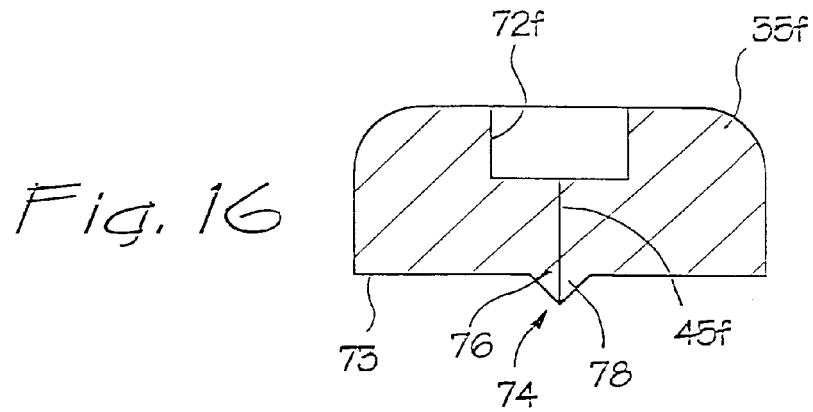
FIG. 16 is an axial cross-section view taken along lines 16-16 of FIG. 15.

A further embodiment of the invention is illustrated in FIGS. 15 and 16 wherein elements of structure similar to those previously described are designated with the same reference numeral followed by the lower case letter "f." As previously discussed with reference to FIG. 12, this embodiment of the pad 35f is formed with a proximal surface 71 and a distal surface 73. The pad 35f also includes the coaxial lead-in cylinder 72f and the trapezoidal slit 45f. However, in this case, a duck-bill valve 74 is provided to further enhance the characteristics of the zero zeal. As illustrated, the working channel 36f is formed by the lead-in cavity 70f, the slit 45f, and an extension of the slit 45f which is defined by the duck-bill valve 74f.

The duck-bill valve 72 can be formed with opposing flanges 76 and 78 which extend distally of the distal surface 73. When operatively disposed, the pad 35f can be positioned with its distal surface 73 against the exterior surface of the abdominal wall 21 (FIG. 2) and with the flanges 76 and 78 extending into the incision 32. With this configuration and operative disposition, the abdominal wall 21 at the incision 32 will produce opposing forces on the flanges 76 and 78 which tend to close the slit 45f, particularly in the absence of an instrument. In this manner, the duck-bill valve 74 can be relied on to enhance the characteristics of the zero seal.

Figure 17:
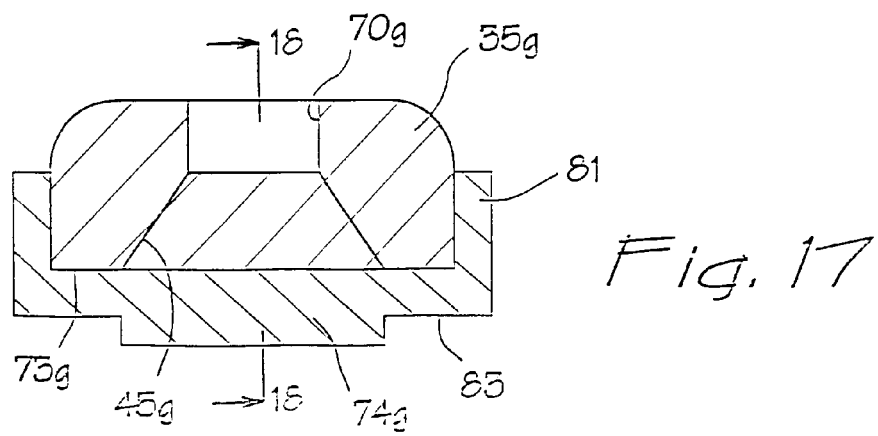
FIG. 17 is a radial cross section view similar to FIG. 13 comprising a softer hand seal and a firmer base seal.
Figure 18:
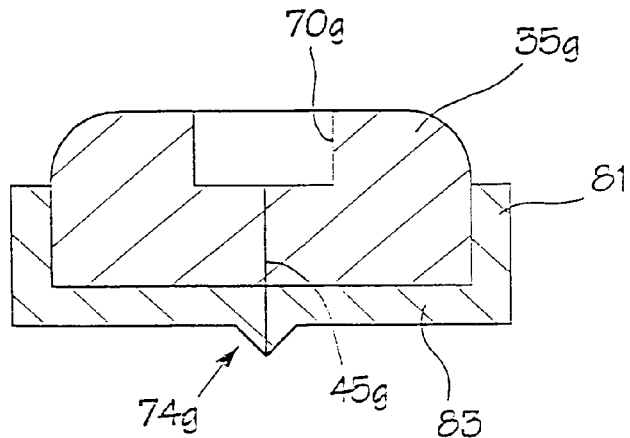
FIG. 18 is an axial cross section view taken along lines 18-18 of FIG. 17.

A further embodiment of the invention is illustrated in FIGS. 17 and 18 wherein elements of structure similar to those previously discussed are designated by the same reference numeral followed by the lower case letter "g." In this embodiment of the access device 34g, the pad 35g can be formed generally as discussed with reference to FIG. 13. In this embodiment, however, the pad 35g can be enclosed along its sides and the distal surface 73g, by a base 81. In this case, the pad 35g might be formed by the highly elastic material previously discussed, while the base 81 might be formed of a more rigid but nevertheless flexible material such as a urethane. With this configuration, the duck-bill valve 74f would be structured to extend distally of a distal surface 83 associated with the base 81. This would enable the duck-bill valve 74f to be formed of the base material rather than the superelastic material. This might also improve the zero seal characteristics for particular operative applications.

Figure 19:
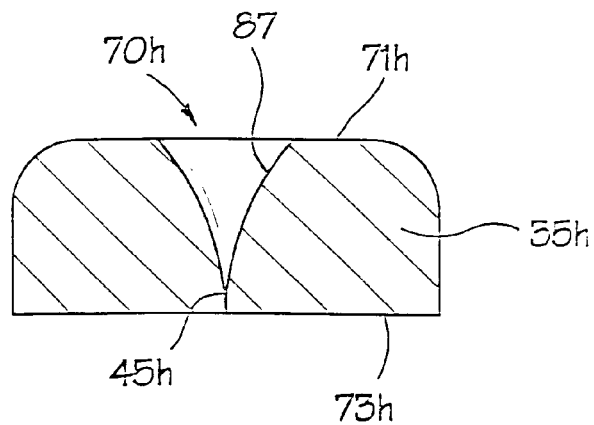
FIG. 19 is an axial cross section view of an embodiment having a lead-in cavity or pocket with a conical or funnel configuration.
Figure 20:
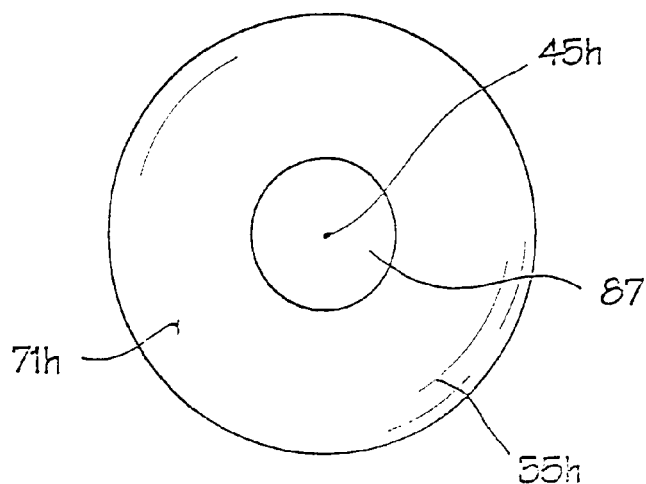
FIG. 20 is a top plan view of the embodiment illustrated in FIG. 19.

Another simplified form of the invention is illustrated in FIGS. 19 and 20, where elements of structure similar to those previously discussed or designated with the same reference numeral followed by the lower case letter "h." The lead-in cavity 78h, in this case, is formed as an inverted cone 77 having its base at the proximal surface 71h and its apex in proximity to the distal surface 73h. Thus, the lead-in cavity 70h has an area in radial cross section which decreases with progressive positions distally through the pad 35h. In this embodiment, the proximal regions near the base of the cone 87 form the instrument seal, while the distal regions at the apex of the cone form the zero seal. The conical configuration of the lead-in cavity 70h also tends to funnel an instrument into the opening 45h leading distally to the apex of the cone 87.

Figure 21:
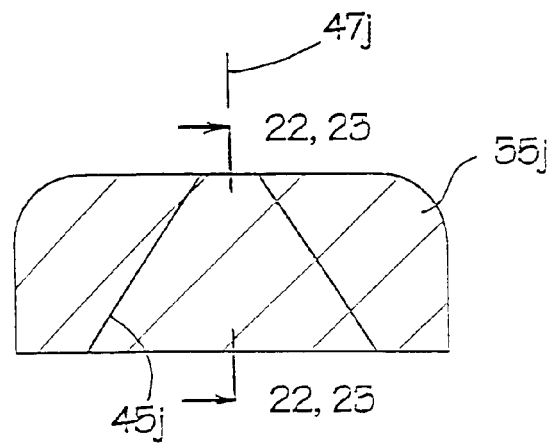
FIG. 21 is an axial cross section view similar to FIG. 13 and showing another embodiment with a trapezoidal slit.
Figure 22:
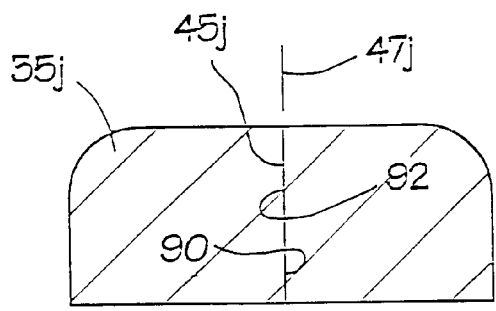
FIG. 22 is an axial cross section view taken along lines 22-22 of FIG. 21.

It will be appreciated generally, that the slit 45 and lead-in cavity 70 can be provided with many different individual and cooperative configurations. By way of example, perhaps the simplest form for the pad 35 is illustrated in the embodiment of FIGS. 21 and 22 wherein elements of structure similar to those previously described are designated by the same reference numeral followed by the lower case letter "j." In this embodiment, the pad 35j with its proximal surface 71j and distal surface 73j, is provided with a simple trapezoidal slit 45j. In this case, the slit 45j extends between the proximal surface 71j and the distal surface 73j.

The slit 45j in this embodiment of FIG. 21 is typical of many structures which will define the slit 45j with a planar configuration. In such a case, the portions of the pad 35j which form the slit will comprise opposing planar surfaces such as those designated by the reference numerals 90 and 92 in FIG. 22.

It will be apparent that the slit 45 need not be formed by opposing surfaces having a planar configuration. Nevertheless, these opposing surfaces need to be capable of coming into sealing contact with each other in order to establish the zero seal. Other slit configurations capable of accomplishing this function, may offer further advantages in particular procedures. Other examples of slit configurations are illustrated merely by way of example in FIGS. 23-26.

Figure 23:
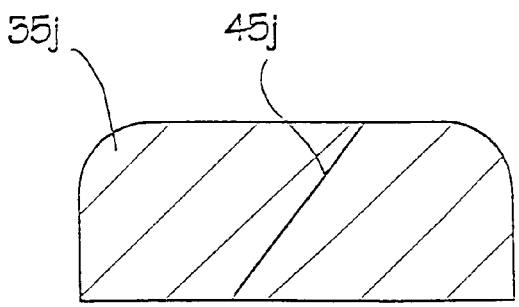
FIG. 23 is an axial cross section view similar to FIG. 22 taken along lines 23-23 of FIG. 21 and illustrating a slit having other than a perpendicular relationship to the plane of the pad.

The embodiment of FIG. 23 is similar to that of FIG. 22 in that the opening 45j comprises a single slit which extends from the proximal surface 71j to the distal surface 73j. In the case of the FIG. 22 embodiment, the axis 47j is disposed within the plane of the slit 45j. In the case of the FIG. 23 embodiment, the plane of the slit 45j does not include the axis 47j. Rather, the slit 45j is formed in a plane which has an angular relationship with the axis 47j, the proximal surface 71j, as well as the distal surface 73j. This construction enables the slit 45j to have a length greater than the thickness of the pad 35j.

Figure 24:
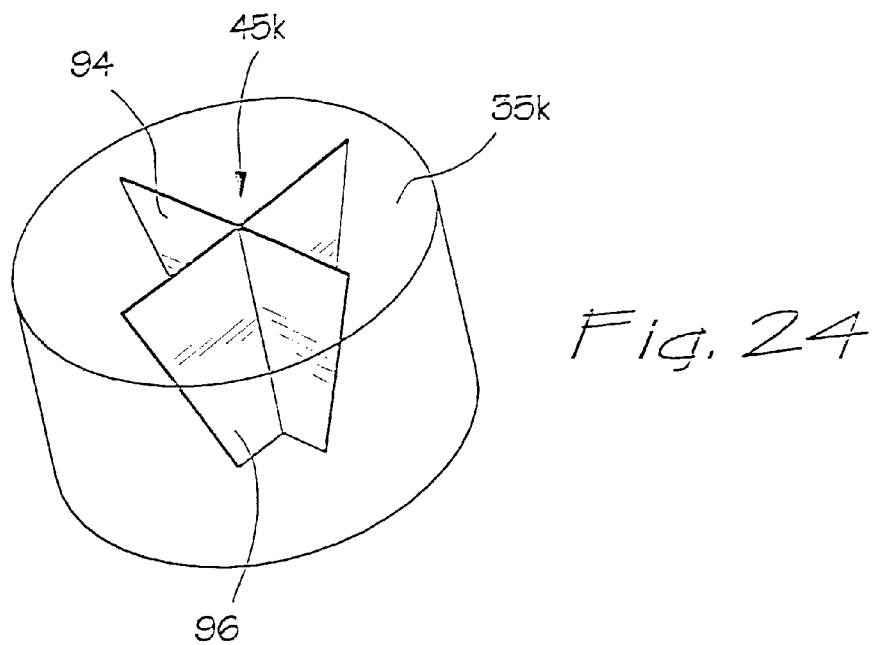
FIG. 24 is a perspective view of a further embodiment of the access device having an opening formed by multiple slits angularly disposed and axially spaced relative to each other.

In the embodiment of FIG. 24, elements of structure similar to those previously discussed are designated with the same reference numeral followed by the lower case letter "k." In this case, the opening 45k is configured as two slits 94 and 96 formed in individual planes that are angularly spaced with respect to each other. Of course, two or more of the planar slit 94 and 96 may be equally angularly spaced around the axis 47k. In one embodiment, the individual planar slits 94 and 96 intersect at the axis 47k. Alternatively, the slits 94 and 96 may be axially spaced in order to facilitate formation of the instrument seal.

Figure 25:
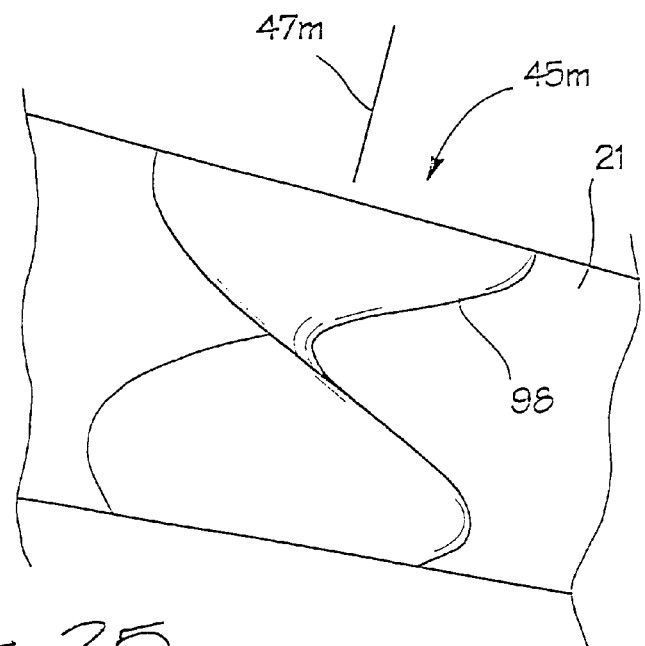
FIG. 25 is a side elevation view of an access device with a slit having a spiral configuration.

In the embodiment of FIG. 25, elements of structure similar to those previously discussed are designated with the same reference numeral followed by the lower case letter "m." In this embodiment, the opening 45m is defined as a slit 98 having a curved rather than planar configuration. In the illustrated embodiment the curved slit 98 is formed as a spiral around the axis 47m. Along the axis 47m, the opposing surfaces forming the spiral slit 98 can "flow" into sealing proximity in order to produce the zero seal.

Figure 26:
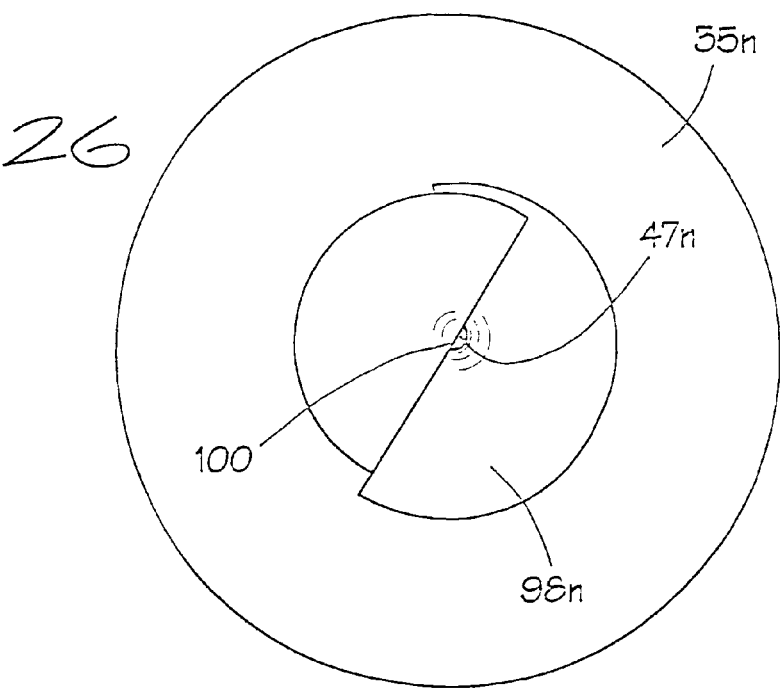
FIG. 26 is a top plan view of an access device having a spiral slit and axial channel.

FIG. 26 illustrates a similar embodiment including a spiral slit. In this figure, elements of structure similar to those previously discussed are designated by the same reference numeral followed by the lower case letter "n." The spiral slit 98n in this embodiment is also formed around the axis 47n of the pad 35n, but in this case the portions forming the slit 98n do not extend completely to the axis 47n. As a result, an axial channel 100 is formed at least, partially along the axis 47n. This channel 100 can function in a manner similar to the lead-in cavity 70 discussed with reference to FIGS. 11-12. This channel 100 can even be formed with a conical configuration similar to that discussed with reference to FIG. 19.

Figure 27:
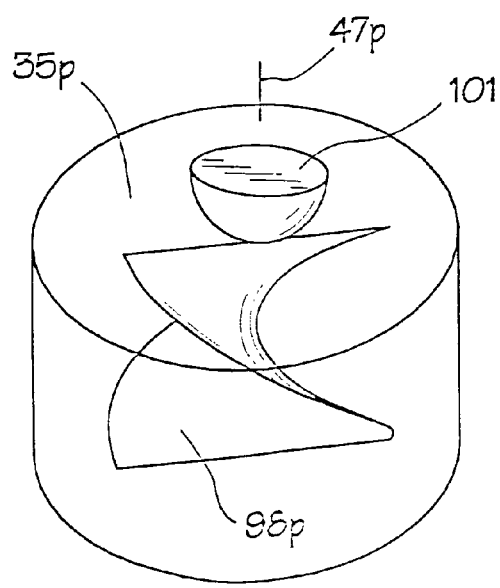
FIG. 27 is a side elevation view of an embodiment having a spiral slit and a septum seal.

In an embodiment where the channel 100 is left open, a zero seal might be provided by positioning a septum valve across the channel 100. Such an embodiment is illustrated in FIG. 27, wherein the septum valve is designated with a reference numeral 101 and the other elements of structure similar to those previously discussed are designated with the same reference numerals followed by the lower case letter "p." Thus the embodiment of FIG. 27 includes the spiral slit 98p, the pad 35p, and the axis 47p. This embodiment of FIG. 27 is merely representative of many other embodiments that will combine a slit, such as the slit 98p, with other valve structures, such as the septum valve 101.

Other curved slit configurations would include embodiments wherein the slit is curved, sinusoidal, or S-shaped in a side elevation view. Such configurations provide a slit part having a length greater than the thickness of the pad. Normally, the more circuitous the slit path, the better the sealing characteristics.

Figure 28:
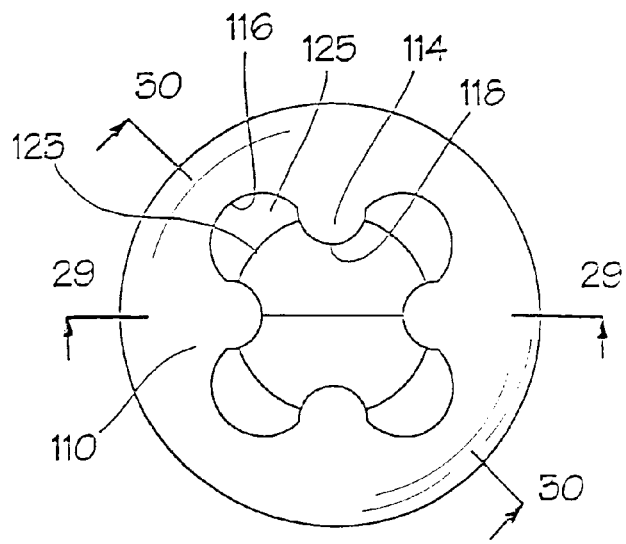
FIG. 28 is an axial cross section view of a further embodiment including a superelastic conical seal and a flexible base with annular spoke-like cams.
Figure 29:
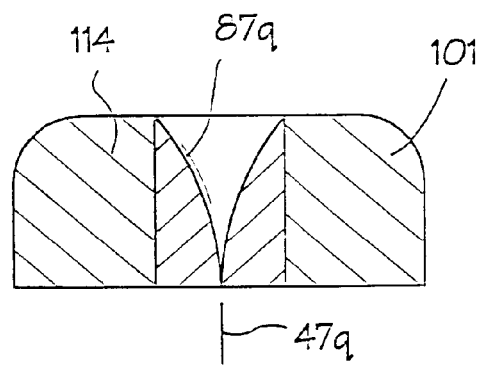
FIG. 29 is an axial cross section view taken along lines 29-29 of FIG. 22.
Figure 30:
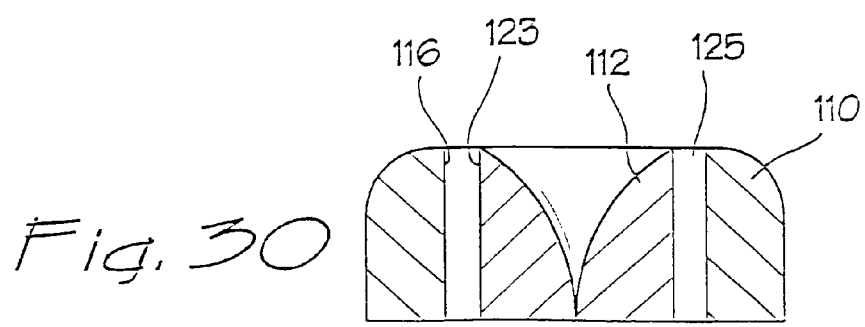
FIG. 30 is an axial cross section view taken along lines 30-30 of FIG. 22.

A further and more complex configuration for the opening 45 is illustrated in the embodiment of FIG. 28 wherein elements of structure similar to those previously disclosed are designated with the same reference numeral followed by the lower case letter "q." This embodiment is representative of many other complex embodiments which can be formed with intricate shapes and different materials in order to accomplish the desirable function of forming, with a single valve, a zero seal as well as an instrument capable of accommodating a full range of instrument sizes. In the embodiment of FIG. 28, the pad 35q is formed with a base 110 which is disposed circumferentially of a core 112. In this case, the core 112 is formed of the superelastic material or gel and provided with the shape of the cone 87q as discussed with reference to FIGS. 19 and 20. The base 110 is formed from a material that may not be elastic, but preferably is flexible. In the preferred embodiment, the base 110 is formed of a urethane.

In this construction, the base 110 is provided with a plurality of spokes 114 each of which extends radially inwardly from a base 116 to a tip 118. The core 112 extends from the axis 47q outwardly to the tips 118 of the spokes 114. In the illustrated embodiment, the core 112 has fingers 121 which extend beyond the tips 118 and toward the bases 116 between each adjacent pair of the spokes 114. These fingers 121 extend radially outwardly to an end surface 123 which stops short of the base 116 leaving a void 125 therebetween.

The voids 125 are of particular interest to this embodiment and can be incorporated into any of the embodiments previously discussed. Such voids 125 provide a space or absence of material into which the highly elastic material, such as that of the fingers 121, can expand during insertion of an instrument such as the arm 16 (FIG. 7). Since the gel material is almost fluid in its properties, the voids 125 permit expansion of the gel with very little resistance. Voids, such as the voids 125 in the embodiment of FIG. 28, can be defined solely in the gel material or between the gel material and any other base material.

Figure 31:
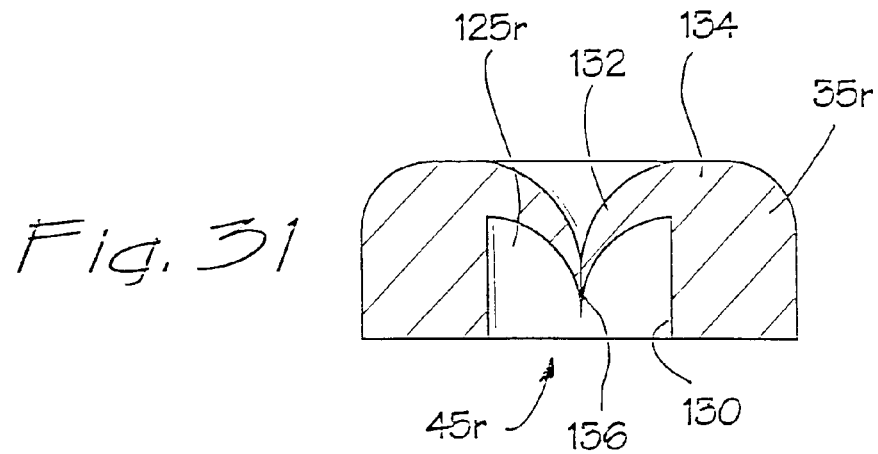
FIG. 31 is an axial cross section view similar to FIG. 28 and illustrating an embodiment including flappers.

In the case of FIG. 28, the spokes 114 and fingers 121 are defined generally in planes which are parallel to the axis 47q. Similar fingers, illustrated in the embodiment of FIG. 31 are defined generally in a plane which is perpendicular to the axis. In this embodiment, elements of structure similar to those previously disclosed are designated by the same reference numeral followed by the lower case letter "r." As illustrated, the pad 35r can be formed with a relatively large opening 45r having the configuration of a coaxial cylinder 130. A plurality of fingers or flaps 132 extend into the opening 45r and tend to form a lead-in cavity 70r with properties such as those discussed with reference to FIG. 19. In this case, the annular flaps 132 have a conical configuration extending from a base 134 to an apex 136. It will be noted that the areas between the flaps 132, form voids 125r into which the flaps 132 can be displaced upon insertion of an instrument, such as the arm 16.

Figure 32:
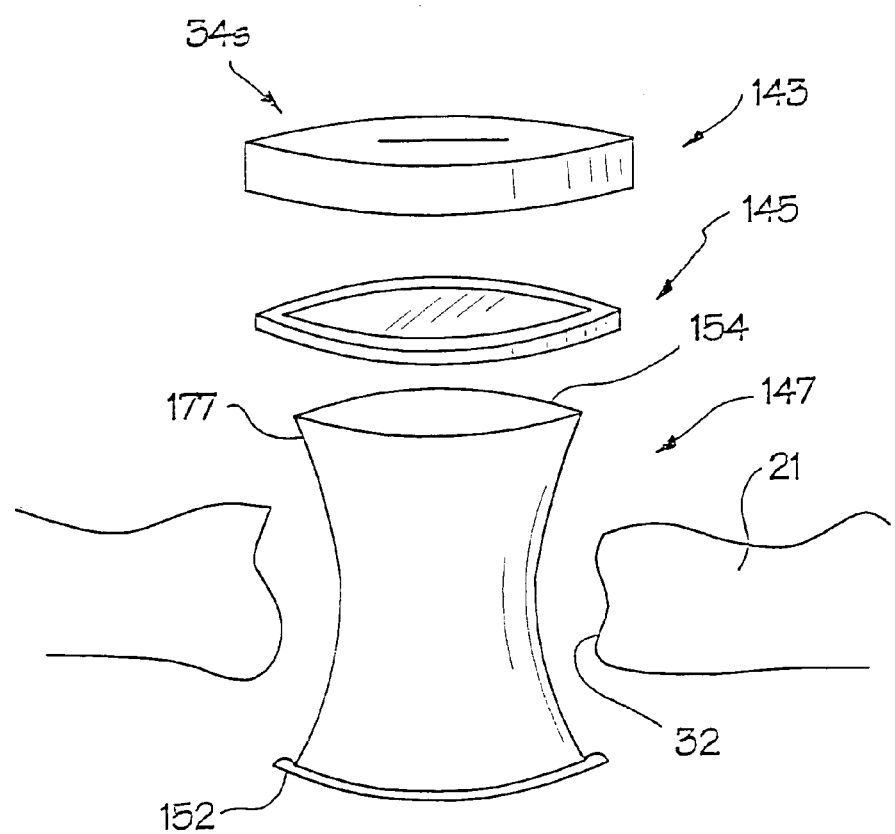
FIG. 32 is a perspective exploded view of a further embodiment including a gel cap, a base, and a retraction sheath.

A further embodiment of the invention is illustrated in FIG. 32 where elements of structure similar to those previously disclosed are designated with the same reference numeral followed by the lower case letter "s." This exploded view of the access device 34s includes not only the pad 35s but also a complimentary structure for maintaining the position of the pad 35s, for forming a seal between the pad 35s and the abdominal wall 21, and for dilating the incision 32 to a variable extent as required by the surgeon 14. In this case, the access device 34s includes three components, a jell cap 143, base 145, and a retraction sheath 147.

The gel cap 143 includes not only the gel pad 35s, but also a circumferential can ring 154 which can be inserted and molded to the pad 35s. The resulting gel cap 143 forms a seal with the base 145, thereby defining the working channel 36s through the pad 35s, the cap ring 154, the base 145, and the retraction sheath 147. In the manner previously discussed, this working channel 36s includes the single valve formed by the gel pad 35s which provides both a zero seal and an instrument seal for a wide range of instrument diameters.

Figure 33:
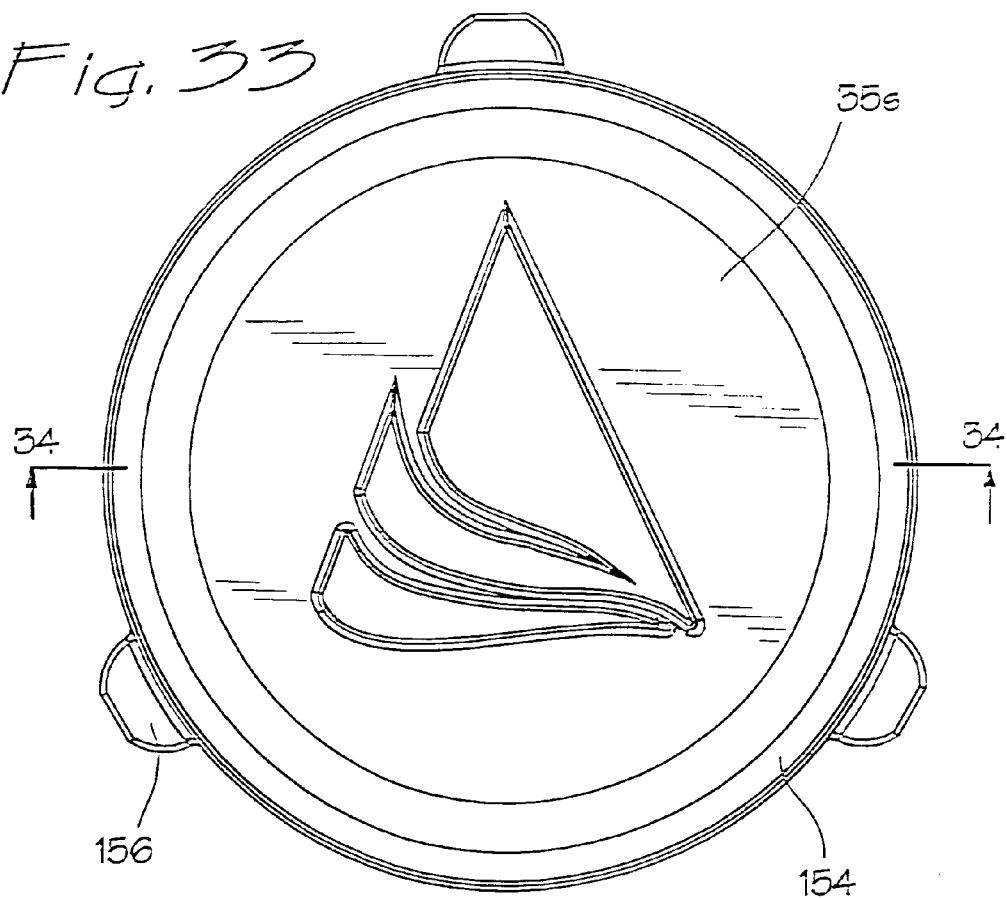
FIG. 33 is a top plan view of the gel cap of FIG. 32.

The structure associated with the gel cap 143 is described in greater detail with reference to FIGS. 33 and 34. In the plan view of FIG. 33, it can be seen that this embodiment includes the gel pad 35s centrally disposed within the circumferential cap ring 154. Holding tabs 156 can be provided to extend radially outwardly of the can ring 154. These holding tabs 156 can facilitate the sealing engagement of the gel cap 143 with the base 145 in the manner described in greater detail below.

The gel pad 35s can be formed of any of the materials previously discussed although the preferred embodiment includes the KRATON/mineral oil gel. The cap ring 154 for such an embodiment can be advantageously formed of KRATON only. This will make the cap ring 154 more rigid than the gel pad 35s while maintaining an excellent material interface between the pad 35s and the ring 154. In a typical manufacturing operation, the cap ring will be pre-disposed in the mold for the gel pad 35s with the unitary structure of the gel cap 143 resulting.

Figure 34:
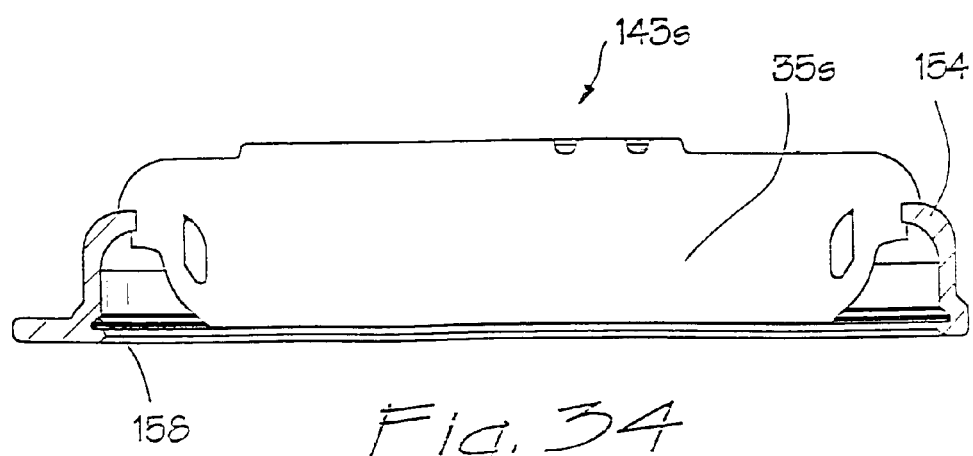
FIG. 34 is an axial cross section view taken along lines 34-34 of FIG. 33.

The cross section view of FIG. 34 shows the gel cap 143s and illustrates an annular void 158 formed on the inner circumference of the cap ring 154. This void 158 is of particular advantage in forming a sealing relationship with the base 145 in the manner discussed in greater detail below.

Figure 35:
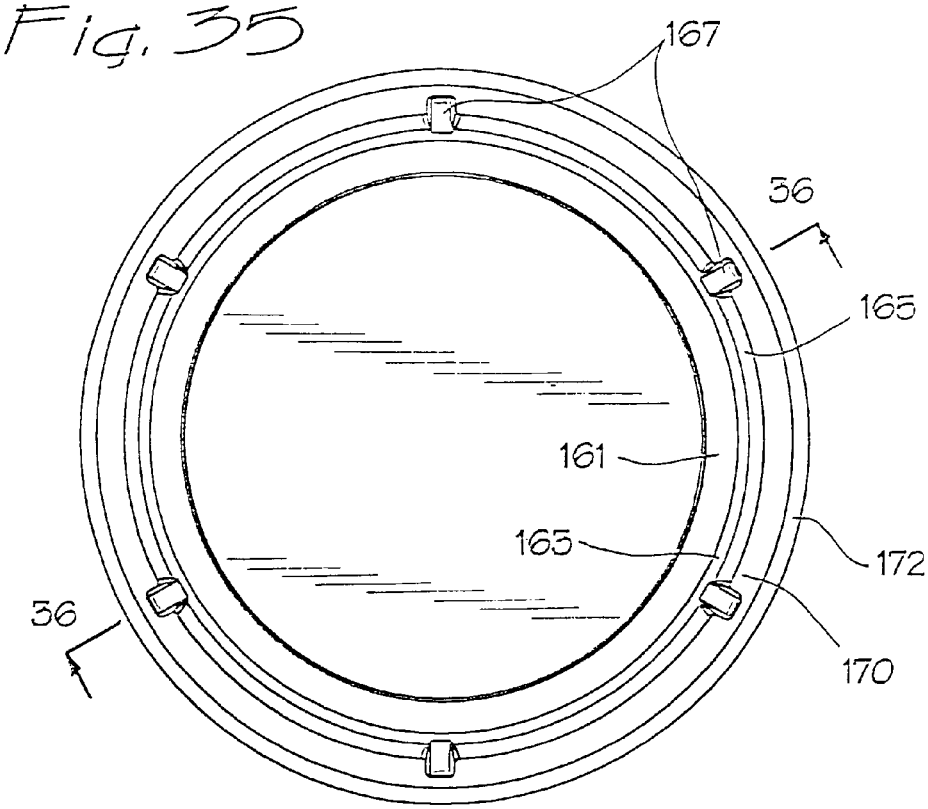
FIG. 35 is a top plan view of the base illustrated in FIG. 32.

The base 145 of this embodiment is shown in greater detail in the plan and cross section of views of FIGS. 34 and 35, respectively. From these views it will be noted that the base 145 can be provided with a smooth generally cylindrical inner surface 161 which extends proximally to a rounded end surface 163 and outwardly from the end surface 163 along an annular lip 165. A plurality of tabs 167 can be equally spaced to extend outwardly and distally around the circumference of the lip 165.

Distally of the inner surface 163, an annular flange 170 can be provided with an annular projection 172 sized and configured to form the desired sealing relationship between the gel can 143 and the base 145. The process of molding the base 145 can be facilitated by forming the base as two separate components divided, for example, by a dotted line 174 in FIG. 35. In a preferred embodiment, the base 145 is molded from a polycarbonate material.

Figure 37:
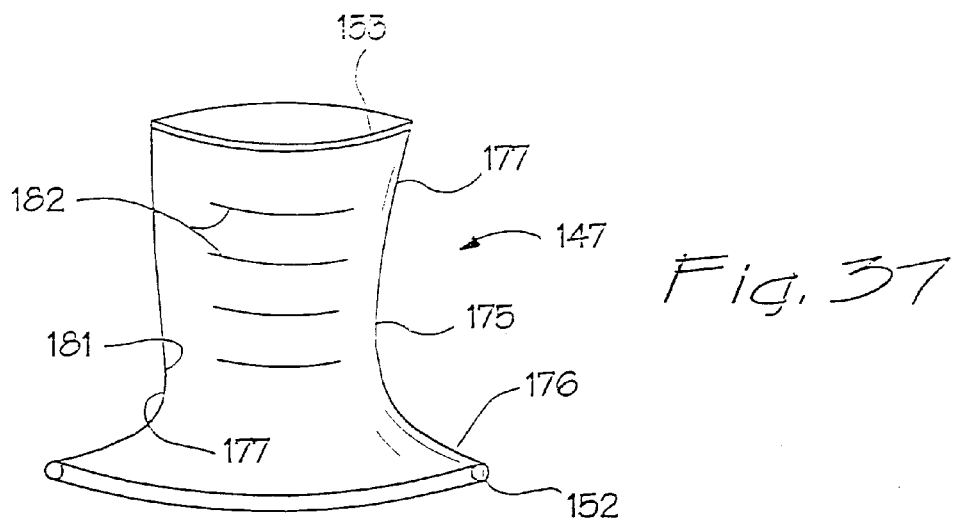
FIG. 37 is a side elevation view of the retraction sheath illustrated in FIG. 32.

A preferred embodiment of the retracting sheath 147 is illustrated in FIG. 37. In this view it can be seen that the retraction sheath 147 includes a tubular wall 175 which has the configuration of the frustum of a cone 176 at its distal end and the configuration of a cylinder 177 at its proximal end. A flexible retaining ring 152 terminates the distal end while a fold 154 is formed at the proximal end. The tubular wall 175 is illustrated to include an outer surface 180 and an inner surface 181. In a preferred embodiment, the sheath 147 is formed of an elastomer, such as neoprene, so its frustule conical and cylindrical configurations exist primarily in the natural unstretched state.

As the sheath 147 is stretched axially, the diameter of the cylindrical proximal end increases thereby placing radial forces on the incision 32. The more the sheath 147 is stretched axially, the greater becomes the diameter of the sheath and consequently the larger becomes the opening through the incision 32. This feature is of particular advantage as it permits the surgeon to define the size of the incision 32 with an appropriate degree of axial tension on the sheath 147. By maintaining this tension, the preferred size of the incision 132 is maintained throughout the operation. In a preferred apparatus and method, the axial tension is maintained by stretching the sheath 147 over the tabs 167 (FIG. 34) of the base 145. Indicia 182 can be printed on the sheath 147 to provide an indication of the relationship between the axial stretch of the sheath 147 and the size of the incision 32.

Figure 38:
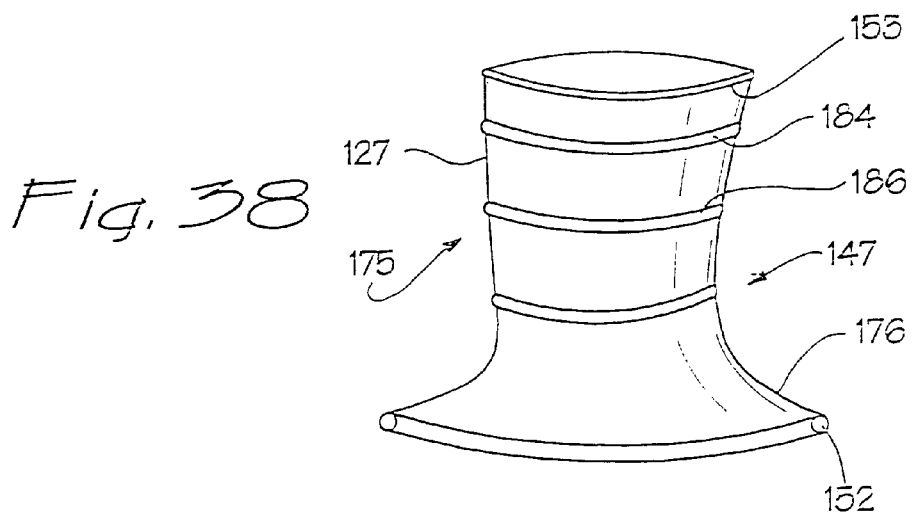
FIG. 38 is a side elevation view of a further embodiment of the retraction sheath.
Figure 39:
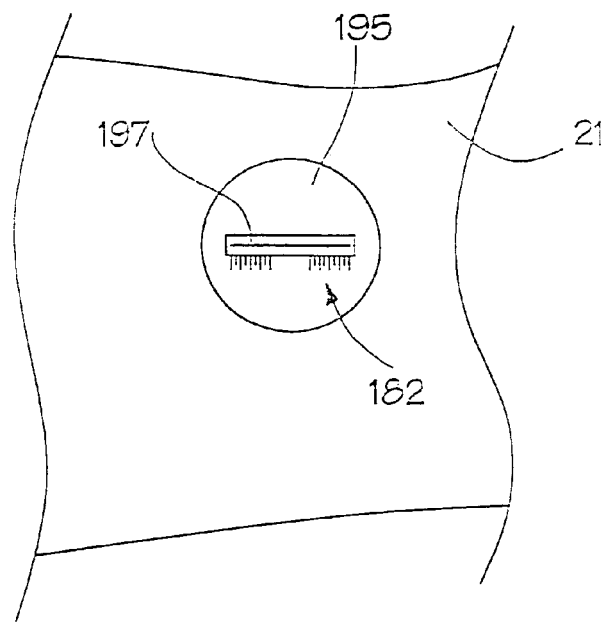
FIGS. 39-42 illustrate progressive steps in a preferred method of use associated with the embodiment of FIG. 32.

The fold 153 is provided to facilitate a grip on the proximal end of the sheath 147. This fold 153 can also function to provide reinforcement where the walls of the sheath 147 engage the tabs 167 of the base 145. In the embodiment illustrated in FIG. 38 additional folds 184, 186 are provided at spaced axial locations, such as those defined by the indicia 182 in FIG. 37. With these folds 184 and 186, additional points of reinforcement are provided to engage the tabs 167 while providing the sheath 147 with predetermined degrees of axial stretch associated with different sizes of the incision 32. The method of using the embodiment of FIG. 32 is illustrated the progressive use of FIGS. 39-42. In FIG. 39, a top plan view of the abdominal wall 21 of the patient 10 is illustrated with a template 195 positioned to facilitate location of the incision 32. The size of the incision 32 can be determined with the indicia 182 on the template 195 showing, for example, multiple lengths of a line 197, each length being equated with a glove size for the surgeon's hand 17 (FIG. 7). Knowing his/her glove size, the surgeon will merely cut the incision in accordance with an appropriate length of the line 197. The longer lengths of the line 197 are associated with the larger incisions, the larger glove sizes and accordingly the larger hands 17. After the incision 32 has been cut along the line 197, the template 195 can be removed.

Figure 40:
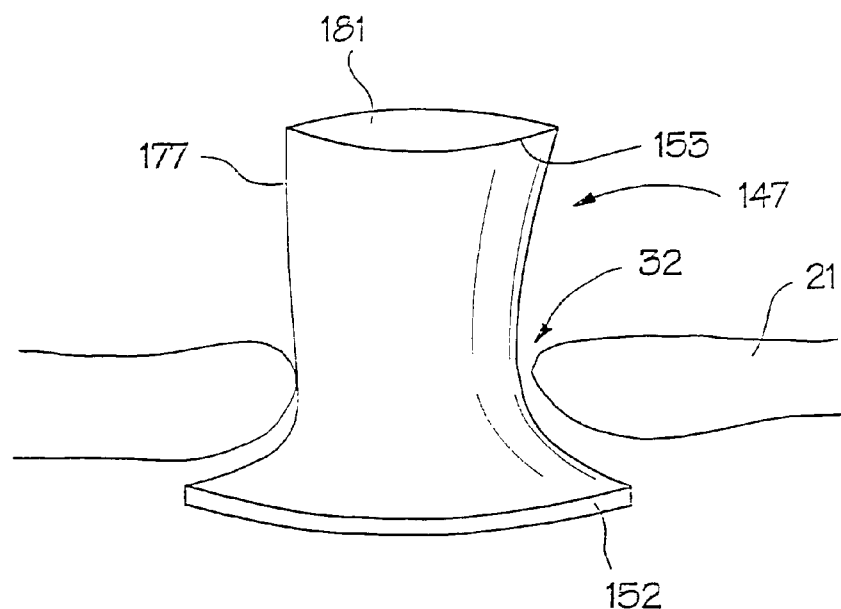

As illustrated in FIG. 40, the retraction sheath 147 can then be mounted through the incision 32. Initially the ring 152 is compressed and fed through the incision 32. On the inner surface of the abdominal wall 21, the ring 152 is free to expand to its larger diameter, as shown by a dotted line 158 in FIG. 40. The portions of the wall 176 which define the cylinder 177 are left to extend proximally through the opening 32 as shown in FIG. 40.

Figure 41:
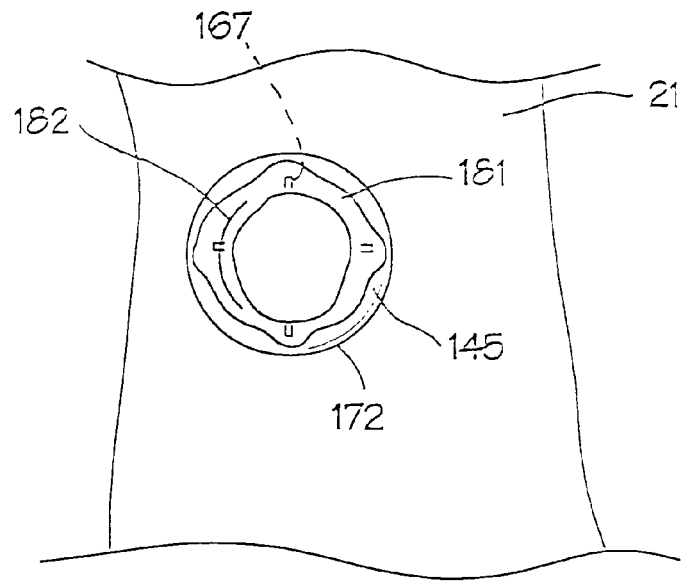
Figure 42:
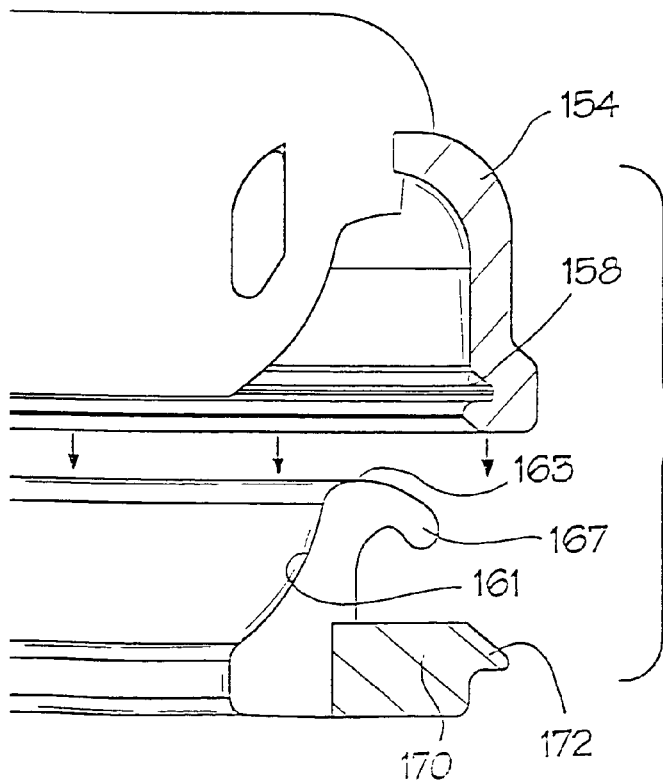

Prior to or after inserting the sheath 147, the base 145 can be disposed around the incision 32. Then the exposed portions of the sheath 147 will extend through the incision 32 and within the circumferential base 145. As illustrated in FIG. 41, the wall 176 of the sheath 147 can then be drawn proximally, outwardly of the page in FIG. 41, to axially stretch the sheath 147. As noted, when the sheath 147 is axially stretched, it will create radial forces on the abdominal wall 21 which will tend to enlarge the incision 32. The greater the axial stretch, the larger the incision 32.

Figure 36:
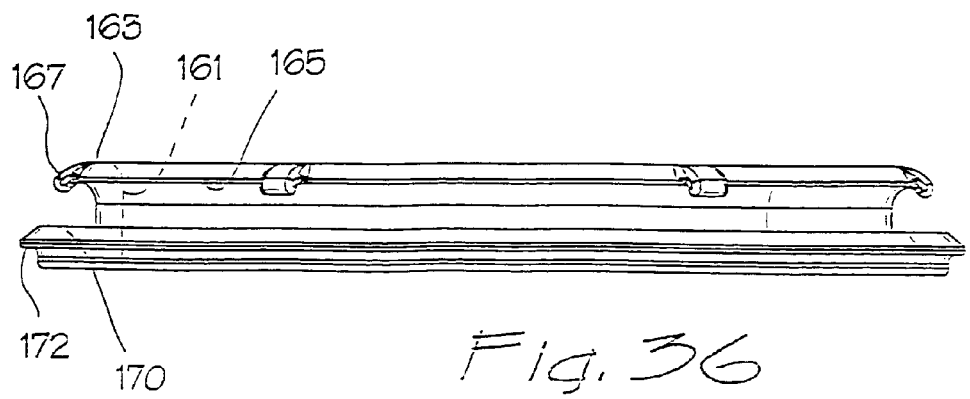
FIG. 36 is an axial cross section view taken along lines 36-36 of FIG. 35.

When the incision 32 has the desired size, the stretched sheath 147 can be drawn over the tabs 167 to maintain the axial stretch and the desired size for the incision 32. Either the indicia 182, as shown in FIG. 36, or the additional folds 184 and 186 as shown in FIG. 37, can be aligned with the tabs 167 to provide a predetermined size for the incision 32. At this point, the seal between the abdominal wall 21, the sheath 147, and the base 145 is fully established.

A final step remaining in this process is the attachment of the gel cap 143 to the base 145. This is accomplished as illustrated in FIG. 36 by capturing the lip 172 of the base 145 in the annular void 158 of the gel cap 143. Bending the holding tabs 156 upwardly and outwardly facilitates this engagement which ultimately forms a seal between the base 145 and the gel cap 143.

Although this invention has been disclosed with reference to certain structural configurations, it will be appreciated that these products are merely representative of many different embodiments of the invention. Accordingly, one is cautioned not to limit the concept only to the disclosed embodiments, but rather encouraged to determine the scope of the invention only with reference to the following claims.

The invention claimed is:

1. A surgical access device for laparoscopic surgical procedures in which an abdominal cavity of a patient is pressurized with an insufflation gas, wherein the access device is adapted to form a sealing relationship with an instrument extending through the access device and into an incision in a body wall of the patient, and is removably connectable to an incision seal support structure comprising a working channel, wherein the incision seal support structure is dimensioned and configured for forming a seal with the body wall of the patient, the incision seal support structure comprising a retaining member dimensioned and configured for insertion through the incision, the access device comprising:

a valve structure comprising an unencapsulated gel material and adapted to be disposed relative to an incision seal support structure, generally closing a proximal end of a working channel thereof;

at least one self-sealing valve included in the unencapsulated gel material of the valve structure, wherein the at least one self-sealing valve is generally aligned with a longitudinal axis of the working channel, and the at least one self-sealing valve has a first state in the absence of an instrument extending through the gel material of the valve structure, and a second state in the presence of an instrument extending through the gel material of the valve structure; and a gel support structure at least partially surrounding and supporting the unencapsulated gel material, wherein the gel support structure is dimensioned and configured for removable coupling to the incision seal support structure, wherein the at least one self-sealing valve in the first state forms a seal in the absence of the instrument extending through the gel material of the valve structure; and the at least one self-sealing valve in the second state forms a seal with the instrument in the presence of the instrument extending through the gel material of the valve structure, wherein the seal with the instrument is formed by direct contact between the gel material and the instrument when the instrument extends through the valve structure.

2. The surgical access device recited in claim 1, wherein the self-sealing valve is dimensioned and configured to accommodate an instrument having a size of an arm of a surgeon.

3. The surgical access device of claim 1, wherein the gel material comprises an elastomeric oil mixture comprising a base; and an oil.

4. The surgical access device of claim 3, wherein the oil comprises at least one of a vegetable oil, a petroleum oil, and a silicone oil.

5. The surgical access device of claim 1, wherein the valve comprises at least one slit.

6. A medical access assembly for laparoscopic surgical procedures in which an abdominal cavity of a patient is pressurized with an insufflation gas, wherein the access assembly is adapted to form a seal with an instrument extending through the assembly and into an incision in a body wall of the patient, and adapted to form a seal with the body wall of the patient, the access assembly comprising:

an incision seal support structure comprising a tubular retraction sheath, a retaining member disposed at a distal portion of the retraction sheath, and a base, wherein the base is dimensioned and configured for coupling to the tubular retraction sheath, the incision seal support structure is dimensioned and configured for retracting an incision and for forming a seal with a body wall of a patient, the retaining member is dimensioned and configured for removable insertion through the incision, and at least one wall of the tubular retraction sheath at least partially defines a working channel sized and configured to receive an instrument when the tubular retraction sheath is positioned within the patient during use;

a gel cap comprising an ultragel coupled to a cap ring, wherein the cap ring is dimensioned and configured for coupling to the base of the incision seal support structure;

an access channel extending through the ultragel and communicating with the working channel, wherein the access channel is adapted to form a seal with an instrument disposed at least in part in the access channel, wherein the gel cap has a first state in the absence of the instrument extending through the access channel, and a second state in the presence of the instrument extending through the access channel, the gel cap in the first state forms a seal in the absence of the instrument extending through the access channel, the gel cap in the second state forms a seal with the instrument in the presence of the instrument extending through the access channel, and the seal with the instrument formed between the ultragel and the instrument when the instrument extends through the access channel.

7. The medical access device recited in claim 6, wherein the ultragel has properties including an elongation of not less than about 1200 percent and a durometer less than about 5 Shore A.

8. The medical access device recited in claim 7, wherein the ultragel has properties including an elongation of not less than about 1500 percent and a durometer of not greater than 200 Bloom.

9. The medical access assembly of claim 6, wherein the gel material comprises an elastomer.

10. The medical access assembly of claim 9, wherein the elastomer comprises at least one of a silicone and a urethane.

11. The medical access assembly of claim 10, wherein the oil comprises at least one of a vegetable oil, a petroleum oil, and a silicone oil.

12. The medical access assembly of claim 9, wherein the elastomer comprises a foam gel comprising a foaming agent and the polyurethane.

13. The medical access assembly of claim 6, wherein the gel comprises at least one of polyurethane, polyvinylchloride, polyisoprene, a thermoset elastomer, a thermoplastic elastomer, a tri-block copolymer, styrene-ethylene/butylene-styrene block copolymer, styrene-isoprene-styrene, styrene-butadiene-styrene, styrene-ethylene/propylene-styrene, an oil, and a foaming agent.

14. The medical access assembly of claim 1, wherein the elastomer comprises an elastomeric oil mixture comprising a base; and an oil.

15. The medical access assembly of claim 1, wherein the access channel comprises at least one slit.

16. The medical access assembly of claim 15, wherein the access channel comprises intersecting slits.

17. The medical access assembly of claim 1, wherein the retaining member comprises a flexible retaining ring.

18. The medical access assembly of claim 1, wherein the retraction sheath in an unstretched state comprises a generally frustoconical distal portion and a generally cylindrical proximal portion.

19. The medical access assembly of claim 1, wherein the retraction sheath comprises an elastomer.

20. The medical access assembly of claim 1, wherein the cap ring is dimensioned and configured for removably coupling to the base of the incision seal support structure.

21. A surgical hand port for laparoscopic surgical procedures in which an abdominal cavity of a patient is pressurized with an insufflation gas, wherein the hand port is adapted for the insertion of a hand of a surgeon through the hand port in a sealing relationship with an arm of the surgeon during laparoscopic surgery through an incision in an abdominal wall of a patient and is adapted for connection to an incision seal support structure comprising a working channel and a retaining member, wherein the incision seal support structure is dimensioned and configured for forming a seal with the abdominal wall of the patient, and the retaining member is dimensioned and configured for insertion through the incision, the hand port comprising:

a valve structure adapted to be disposed relative to an incision seal support structure to generally close a proximal end of a working channel of the incision seal support structure, the valve structure comprising a gel material;

a valve included in the gel material of the valve structure defining a sealable opening adapted to provide access through the incision; and a gel support structure at least partially surrounding and supporting the gel material, wherein the gel support structure is configured for connection to the incision seal support structure, wherein the gel material is configured for sealing the opening in the absence of any object extending through the opening, and for sealing the opening around an arm of a surgeon extending through the opening, the seal with the surgeon's arm being formed between the gel material and the surgeon's arm when the surgeon's arm is extending through the opening; and the gel material comprises an elastomeric oil mixture.

22. The surgical access device recited in claim 21, wherein the elastomeric oil mixture has properties including an elongation greater than about 1000 percent.

23. The surgical access device recited in claim 21, wherein the elastomeric oil mixture has a durometer less than about 5 Shore A.

* * * * *